United States Patent
Zhang et al.

(10) Patent No.: US 9,487,545 B2
(45) Date of Patent: Nov. 8, 2016

(54) FUSED RING-CONTAINING OXAZOLIDINONES ANTIBIOTICS

(71) Applicant: Xuanzhu Pharma Co., Ltd., Shandong (CN)

(72) Inventors: Hui Zhang, Shandong (CN); Aichen Wang, Shandong (CN)

(73) Assignee: Xuanzhu Pharma Co., Ltd., Shandong (CN)

( * ) Notice: Subject to any disclaimer, the term of this patent is extended or adjusted under 35 U.S.C. 154(b) by 104 days.

(21) Appl. No.: 14/347,595

(22) PCT Filed: Sep. 29, 2012

(86) PCT No.: PCT/CN2012/082422
§ 371 (c)(1),
(2) Date: Mar. 26, 2014

(87) PCT Pub. No.: WO2013/044865
PCT Pub. Date: Apr. 4, 2013

(65) Prior Publication Data
US 2014/0243288 A1 Aug. 28, 2014

(30) Foreign Application Priority Data
Sep. 30, 2011 (CN) .......................... 2011 1 0291417

(51) Int. Cl.
| | | |
|---|---|---|
| C07D 491/048 | (2006.01) |
| C07D 413/14 | (2006.01) |
| C07D 487/04 | (2006.01) |
| C07D 495/04 | (2006.01) |
| C07F 9/6558 | (2006.01) |
| C07F 9/6561 | (2006.01) |
| C07D 498/04 | (2006.01) |
| C07D 513/04 | (2006.01) |
| C07D 405/14 | (2006.01) |

(52) U.S. Cl.
CPC ........... *C07F 9/6561* (2013.01); *C07D 405/14* (2013.01); *C07D 413/14* (2013.01); *C07D 487/04* (2013.01); *C07D 491/048* (2013.01); *C07D 495/04* (2013.01); *C07D 498/04* (2013.01); *C07D 513/04* (2013.01); *C07F 9/65583* (2013.01)

(58) Field of Classification Search
None
See application file for complete search history.

(56) References Cited

U.S. PATENT DOCUMENTS

2011/0098471 A1    4/2011    Katoh et al.

FOREIGN PATENT DOCUMENTS

| CN | 102190656 | 9/2011 |
| CN | 103030634 A | 4/2013 |
| JP | 2003516404 A | 5/2003 |
| JP | 2004518724 A | 6/2004 |
| JP | 2005520815 A | 7/2005 |
| WO | WO-96/35691 | 11/1996 |
| WO | WO-0142242 | 6/2001 |
| WO | WO-2007114326 A1 | 10/2007 |
| WO | WO-2009157423 | 12/2009 |
| WO | WO-2011097946 | 8/2011 |

*Primary Examiner* — Kamal Saeed
(74) *Attorney, Agent, or Firm* — Cesari and McKenna LLP

(57) ABSTRACT

The present invention relates to a fused ring-containing oxazolidinone compound shown by general formula (I), a pharmaceutically acceptable salt thereof and a stereoisomer thereof, wherein $R^1$, $R^2$, $R^3$, $R^4$, $R^5$, $R^6$, A, B and C are as defined in the description. The present invention further relates to a method for preparing the compound, a pharmaceutical composition and a pharmaceutical formulation comprising the compound, and a use of the compound for the manufacture of a medicament for the treatment and/or prevention of infectious diseases and a use for the treatment and/or prevention of infectious diseases.

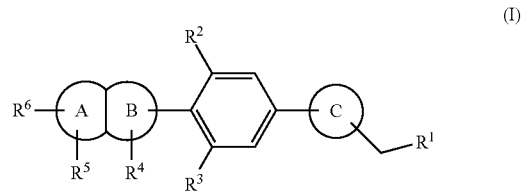

(I)

10 Claims, No Drawings

FUSED RING-CONTAINING OXAZOLIDINONES ANTIBIOTICS

CROSS REFERENCE TO RELATED APPLICATIONS

This application is the national stage entry under 35 USC 371 for PCT/CN2012/082422, filed on Sep. 29, 2012, which claims the benefit of the Sep. 30, 2011 priority date of Chinese Application No. 201110291417.4. The contents of the foregoing applications are incorporated herein by reference.

1. Technical Field

The present invention relates to the technical field of pharmaceuticals, and specifically to a fused ring-containing oxazolidinones antibiotic, a pharmaceutically acceptable salt thereof, an isomer thereof and a prodrug thereof, a method for preparing the compound, a pharmaceutical composition and a pharmaceutical formulation comprising the compound, a use of the compound for the manufacture of a medicament useful for the treatment and/or prevention of infectious diseases and a use of the compound for the treatment and/or prevention of infectious diseases.

2. Background

Oxazolidinones antibiotics are a novel class of completely chemically synthesized antibiotics with effects of inhibiting multidrug resistant Gram-positive bacteria developed following sulfonamides and fluoroquinolones.

Linezolid is the first oxazolidinones antibiotic in the market.

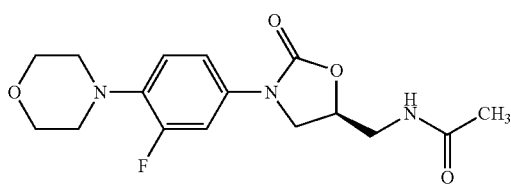 [SMILES: CC(=O)NC[C@H]1CN(c2ccc(N3CCOCC3)c(F)c2)C(=O)O1]

Linezolid has relatively strong effects of inhibiting Gram-positive bacteria and does not have cross resistance with other antibiotics. Linezolid has a unique mechanism of action and can inhibit the early phase of the synthesis of bacterioprotein. Linezolid is mainly used for treating infectious diseases induced by resistant Gram-positive bacteria, and can also be used for treating surgical infectious diseases.

US2011098471 discloses Compound 38 as below, for Gram-positive bacteria induced infectious diseases.

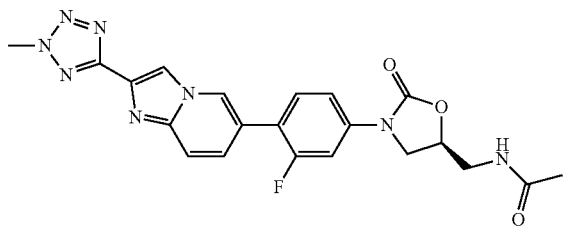 [SMILES: CC(=O)NC[C@H]1CN(c2ccc(-c3ccc4nc(-c5nnn(C)n5)cn4c3)c(F)c2)C(=O)O1]

However, resistance of Gram-positive bacteria is getting more and more serious clinically. Oxazolidinones antibiotics have a very limited variety of pharmaceuticals for clinical use, currently with only linezolid in the market, and cannot meet the clinical needs. In addition, the resistance to linezolid is getting more and more serious. Thus, there is an urgent need to expand varieties of clinically used oxazolidinones antibiotics, and develop antibiotics highly effective against resistant Gram-positive bacteria.

3. Summary of the Invention

In order to meet clinical needs, the present invention provides a class of anti-infective compounds having a relatively high antibiotic activity. Specific embodiments are as follows:

A compound shown by general formula (I), a pharmaceutically acceptable salt thereof, an isomer thereof or a prodrug thereof:

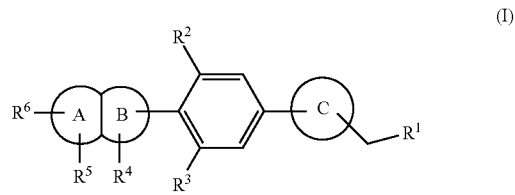

wherein, $R^1$ is selected from (1) —$OR^7$, (2) —$NR^7R^{7'}$, (3) —$COR^7$, (4) —$COOR^7$, (5) —$OCOR^7$, (6) —$CONR^7R^{7'}$, (7) —$NR^7COR^{7'}$, (8) —$OCONR^7R^{7'}$, (9) —$NR^7COOR^{7'}$, (10) —$NR^7CONR^7R^7$, (11) —$CSR^7$, (12) —$CSOR^7$, (13) —$OCSR^7$, (14) —$CSNR^7R^{7'}$, (15) —$NR^7CSR^{7'}$, (16) —$OCSNR^7R^{7'}$, (17) —$NR^7CSOR^{7'}$, (18) —$NR^7CSNR^7R^{7'}$, (19) —$NR^7C(NR^7)NR^7R^{7'}$, (20) —$S(O)_pR^7$, (21) —$SO_2NR^7R^{7'}$, or (22) $R^7$, p is 0, 1 or 2, $R^7$, $R^{7'}$ are selected from: (1) H, (2) $C_{1-6}$ alkyl, (3) $C_{2-6}$ alkenyl, (4) $C_{2-6}$ alkynyl, (5) 3-14 membered cycloalkyl or 6-14 membered aryl, (6) 3-14 membered heterocyclyl containing one or more heteroatoms selected from N, S, O and/or $SO_2$, (7) —$COC_{1-6}$ alkyl, (8) —$COC_{2-6}$ alkenyl, or (9) —$COC_{2-6}$ alkynyl;

$R^2$, $R^3$ are independently selected from hydrogen, halogen, $C_{1-6}$ alkyl, $C_{1-6}$ alkylamino, di($C_{1-6}$ alkyl)amino or $C_{1-6}$ alkoxyl;

is a fused condensed bicyclic system formed by ring A and ring B together, wherein ring A is selected from 3-8 membered cyclic group, which is unsubstituted or substituted by 1-3 $R^5$, wherein $R^5$ is independently selected from hydrogen, halogen, $C_{1-6}$ alkyl, halo$C_{1-6}$ alkyl, hydroxyl, hydroxyl$C_{1-6}$ alkyl, amino, $C_{1-6}$ alkylamino, di($C_{1-6}$ alkyl)amino or $C_{1-6}$ alkylcarbamyl;

ring B is selected from phenyl ring or 5 membered heteroaryl, which are unsubstituted or substituted by 1-3 $R^4$, wherein $R^4$ is independently selected from hydrogen, halogen, $C_{1-6}$ alkyl, halo$C_{1-6}$ alkyl, hydroxyl, hydroxyl$C_{1-6}$ alkyl, amino, $C_{1-6}$ alkylamino, di($C_{1-6}$ alkyl)amino or $C_{1-6}$ alkylcarbamyl;

ring C is selected from

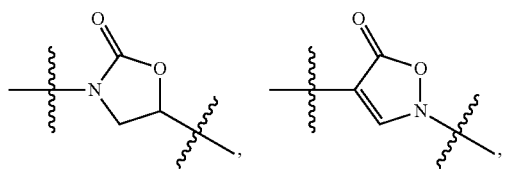

-continued

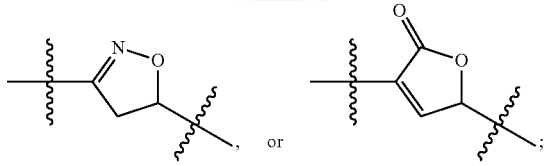

R⁶ is selected from the following groups, which are unsubstituted or substituted by 1-3 R⁸:
(1) 3-14 membered cycloalkyl or 6-14 membered aryl,
(2) 3-14 membered heterocyclyl, or
(3) 5-14 membered heteroaryl,
R⁸ is selected from halogen, carboxyl, hydroxyl, amino, cyano, nitro, $C_{1-6}$ alkyl, carboxyl$C_{1-6}$ alkyl, hydroxyl$C_{1-6}$ alkyl, amino$C_{1-6}$ alkyl, halo$C_{1-6}$ alkyl, $C_{1-6}$ alkoxyl, halo$C_{1-6}$ alkoxyl, $C_{1-6}$ alkoxyl$C_{1-6}$ alkyl, $C_{1-6}$ alkylamino, di($C_{1-6}$ alkyl)amino, di($C_{1-16}$ alkyl)amino$C_{1-6}$ alkyl, $C_{1-6}$ alkyl-carbonyl, $C_{1-6}$ alkylcarbonyloxy, $C_{1-6}$ alkoxylcarbonyl, carbamyl, carbamyl$C_{1-6}$ alkyl, $C_{1-6}$ alkylcarbamyl, di($C_{1-6}$ alkyl)carbamyl, aminosulfonyl, aminosulfonyl$C_{1-6}$ alkyl, $C_{1-6}$ alkylaminosulfonyl, di(C alkyl)aminosulfonyl, $C_{1-6}$ alkylsulfonylamino, $C_{1-6}$ alkylsulfonyl, $C_{1-6}$ alkylcarbonylamino or guanidino.

Preferably is:
wherein,
R¹ is selected from acetylamino, hydroxyl, 1,2,3-triazolyl or isoxazolyloxy;
R², R³ are independently selected from hydrogen or halogen;
ring A is selected from 5-6 membered cycloalkyl or 5-6 membered heterocyclyl, which are unsubstituted or substituted by 1-2 R⁵, wherein R⁵ is independently selected from hydrogen, halogen, $C_{1-4}$ alkyl, halo$C_{1-4}$ alkyl, hydroxyl, hydroxyl$C_{1-4}$ alkyl, amino, $C_{1-4}$ alkylamino, di($C_{1-4}$ alkyl) amino or $C_{1-4}$ alkylcarbamyl;
ring B is selected from phenyl ring or 5 membered heteroaryl, which are unsubstituted or substituted by 1-2 R⁴, wherein R⁴ is independently selected from hydrogen, halogen, $C_{1-4}$ alkyl, halo$C_{1-4}$ alkyl, hydroxyl, hydroxyl$C_{1-4}$ alkyl, amino, $C_{1-4}$ alkylamino, di($C_{1-4}$ alkyl)amino or $C_{1-4}$ alkylcarbamyl;
R⁶ is selected from 5-6 membered heteroaryl containing 1, 2, 3 or 4 N atoms, which is unsubstituted or substituted by 1-2 R⁸, wherein R⁸ is selected from $C_{1-4}$ alkyl which is unsubstituted or substituted by halogen.

Preferably is:
wherein,
R¹ is acetylamino or hydroxyl;
R², R³ are independently selected from hydrogen or fluoro;
ring A is selected from the following groups, which are unsubstituted or substituted by 1-2 R⁵: cyclopentyl, cyclohexyl, tetrahydropyrrolyl, 2,3-dihydropyrrolyl, 2,5-dihydropyrrolyl, pyrrolyl, imidazolyl, 4,5-dihydroimidazolyl, pyrazolyl, 4,5-dihydropyrazolyl, 1,2,3-triazolyl, tetrahydrothienyl, thienyl, 2,3-dihydrothienyl, thiazolyl, 4,5-dihydrothiazolyl, isothiazolyl, tetrahydrofuryl, 2,3-dihydrofuryl, furyl, 4,5-dihydrooxazolyl, oxazolyl, 4,5-dihydroisoxazolyl, isoxazolyl, phenyl ring, 1,4,5,6-tetrahydropyrimidinyl, 1,6-dihydropyrimidinyl, 4,5-dihydropyrimidinyl, pyrimidinyl, 3,6-dihydro-2H-pyranyl, 2H-pyranyl, piperidyl, 1,2,3,4-tetrahydropyridyl, 1,2,3,6-tetrahydropyridyl, 2,3-dihydropyridyl, pyridyl, piperazinyl, 1,2,3,4-tetrahydropyrazinyl, 2,3-dihydropyrazinyl or pyrazinyl group, wherein R⁵ is independently selected from hydrogen, fluoro, methyl, trifluoromethyl, hydroxyl, hydroxylmethyl, amino, methylamino, ethylamino, methylcarbamyl or ethylcarbamyl;
ring B is selected from phenyl ring or 5 membered heteroaryl, which are unsubstituted or substituted by 1-2 R⁴, wherein R⁴ is independently selected from hydrogen, fluoro, methyl, fluoromethyl, trifluoromethyl, hydroxyl, hydroxylmethyl, amino, methylamino, ethylamino, methylcarbamyl or ethylcarbamyl;
R⁶ is selected from the following groups, which are unsubstituted or substituted by 1-2 R⁸: pyrrolyl, imidazolyl, pyrazolyl, 1,2,3-triazolyl, 1,2,4-triazolyl, 1,2,3,4-tetrazolyl, pyridyl or pyrazinyl, wherein R⁸ is selected from methyl, ethyl, propyl or trifluoromethyl.

Further preferably is:
wherein,
R¹ is acetylamino or hydroxyl;
R², R³ are independently selected from hydrogen or fluoro;
ring A is selected from the following groups, which are unsubstituted or substituted by 1-2 R⁵: cyclopentyl, cyclohexyl, tetrahydropyrrolyl, 2,3-dihydropyrrolyl, 2,5-dihydropyrrolyl, pyrrolyl, imidazolyl, 4,5-dihydroimidazolyl, pyrazolyl, 4,5-dihydropyrazolyl, 1,2,3-triazolyl, tetrahydrothienyl, thienyl, 2,3-dihydrothienyl, thiazolyl, 4,5-dihydrothiazolyl, isothiazolyl, tetrahydrofuryl, 2,3-dihydrofuryl, furyl, 4,5-dihydrooxazolyl, oxazolyl, 4,5-dihydroisoxazolyl, isoxazolyl, phenyl ring, 1,4,5,6-tetrahydropyrimidinyl, 1,6-dihydropyrimidinyl, 4,5-dihydropyrimidinyl, pyrimidinyl, 3,6-dihydro-2H-pyranyl, 2H-pyranyl, piperidyl, 1,2,3,4-tetrahydropyridyl, 1,2,3,6-tetrahydropyridyl, 2,3-dihydropyridyl, pyridyl, piperazinyl, 1,2,3,4-tetrahydropyrazinyl, 2,3-dihydropyrazinyl or pyrazinyl group, wherein R⁵ is independently selected from hydrogen, fluoro, methyl, trifluoromethyl, hydroxyl, hydroxylmethyl, amino, methylamino, ethylamino, methylcarbamyl or ethylcarbamyl;
ring B is selected from phenyl ring, thiazolyl, imidazolyl, thienyl, furyl, pyrazolyl, pyrrolyl, 1,2,3-triazolyl, 1,2,4-triazolyl, 1,2,3,4-tetrazolyl, oxazolyl, which are unsubstituted or substituted by 1-2 R⁴, wherein R⁴ is independently selected from hydrogen, fluoro, methyl, fluoromethyl, trifluoromethyl, hydroxyl, hydroxylmethyl, amino, methylamino, ethylamino, methylcarbamyl or ethylcarbamyl;
R⁶ is selected from the following groups, which are unsubstituted or substituted by 1-2 R⁸: pyrrolyl, imidazolyl, pyrazolyl, 1,2,3-triazolyl, 1,2,4-triazolyl, 1,2,3,4-tetrazolyl, pyridyl or pyrazinyl, wherein R⁸ is selected from methyl, ethyl, propyl or trifluoromethyl.

Further preferably is:
wherein,
R¹ is acetylamino or hydroxyl;
R², R³ are independently selected from hydrogen or fluoro;
ring A is selected from the following groups, which are unsubstituted or substituted by 1-2 R⁵: cyclopentyl, cyclohexyl, tetrahydropyrrolyl, 2,3-dihydropyrrolyl, 2,5-dihydropyrrolyl, pyrrolyl, imidazolyl, 4,5-dihydroimidazolyl, pyrazolyl, 4,5-dihydropyrazolyl, 1,2,3-triazolyl, tetrahydrothienyl, thienyl, 2,3-dihydrothienyl, thiazolyl, 4,5-dihydrothiazolyl, tetrahydrofuryl, 2,3-dihydrofuryl, furyl, oxazolyl, phenyl ring, 1,4,5,6-tetrahydropyrimidinyl, 1,6-dihydropyrimidinyl, 4,5-dihydropyrimidinyl, pyrimidinyl, 3,6-dihydro-2H-pyranyl, 2H-pyranyl, piperidyl, 1,2,3,4-tetrahydropyridyl, 1,2,3,6-tetrahydropyridyl, 2,3-dihydropyridyl, pyridyl, piperazinyl, 1,2,3,4-tetrahydropyrazinyl, 2,3-dihydropyrazinyl or pyrazinyl group, wherein $R^5$ is selected from hydrogen, fluoro, methyl or methylcarbamyl;

ring B is selected from phenyl ring, thiazolyl, imidazolyl, thienyl, furyl, pyrazolyl, pyrrolyl, 1,2,3-triazolyl, 1,2,4-triazolyl, oxazolyl, which are unsubstituted or substituted by 1-2 $R^4$, wherein $R^4$ is selected from hydrogen, fluoro, methyl or fluoromethyl;

$R^6$ is selected from 1,2,3-triazolyl, 1,2,4-triazolyl or 1,2,3,4-tetrazolyl, which are unsubstituted or substituted by 1-2 $R^8$, wherein $R^8$ is selected from methyl or ethyl.

Another embodiment of the present invention is as follows:

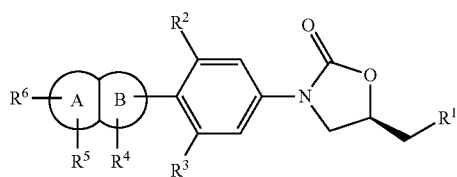

(II)

wherein, $R^1$ is selected from (1) —$OR^7$, (2) —$NR^7R^{7'}$, (3) —$COR^7$, (4) —$COOR^7$, (5) —$OCOR^7$, (6) —$CONR^7R^{7'}$, (7) —$NR^7COR^{7'}$, (8) —$OCONR^7R^{7'}$, (9) —$NR^7COOR^{7'}$, (10) —$NR^7CONR^7R^{7'}$, (11) —$CSR^7$, (12) —$CSOR^7$, (13) —$OCSR^7$, (14) —$CSNR^7R^{7'}$, (15) —$NR^7CSR^{7'}$, (16) —$OCSNR^7R^{7'}$, (17) —$NR^7CSOR^{7'}$, (18) —$NR^7CSNR^7R^{7'}$, (19) —$NR^7C(NR^7)NR^7R^{7'}$, (20) —$S(O)_pR^7$, (21) —$SO_2NR^7R^{7'}$, or (22) $R^7$, p is 0, 1 or 2, $R^7$, $R^{7'}$ are selected from: (1) H, (2) $C_{1-6}$ alkyl, (3) $C_{2-6}$ alkenyl, (4) $C_{2-6}$ alkynyl, (5) 3-14 membered cycloalkyl or 6-14 membered aryl, (6) 3-14 membered heterocyclyl containing one or more heteroatoms selected from N, S, O and/or $SO_2$, (7) —$OCC_{1-6}$ alkyl, (8) —$COC_{2-6}$ alkenyl, or (9) —$COC_{2-6}$ alkynyl;

$R^2$, $R^3$ are independently selected from hydrogen, halogen, $C_{1-6}$ alkyl, $C_{1-6}$ alkylamino, alkyl)amino or $C_{1-6}$ alkoxyl;

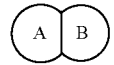

is a fused condensed bicyclic system formed by ring A and ring B together, wherein ring A is selected from 3-8 membered cyclic group, which is unsubstituted or substituted by 1-3 $R^5$, wherein $R^5$ is independently selected from hydrogen, halogen, $C_{1-6}$ alkyl, halo$C_{1-6}$ alkyl, hydroxyl, hydroxyl$C_{1-6}$ alkyl, amino, $C_{1-6}$ alkylamino, di($C_{1-6}$ alkyl)amino or $C_{1-6}$ alkylcarbamyl;

ring B is selected from phenyl ring or 5 membered heteroaryl, which are unsubstituted or substituted by 1-3 $R^4$, wherein $R^4$ is independently selected from hydrogen, halogen, $C_{1-6}$ alkyl, halo$C_{1-6}$ alkyl, hydroxyl, hydroxyl$C_{1-6}$ alkyl, amino, $C_{1-6}$ alkylamino, di($C_{1-6}$ alkyl)amino or $C_{1-6}$ alkylcarbamyl;

$R^6$ is selected from the following groups, which are unsubstituted or substituted by 1-3 $R^8$:
(1) 3-14 membered cycloalkyl or 6-14 membered aryl,
(2) 3-14 membered heterocyclyl, or
(3) 5-14 membered heteroaryl, $R^8$ is selected from halogen, carboxyl, hydroxyl, amino, cyano, nitro, $C_{1-6}$ alkyl, carboxyl$C_{1-6}$ alkyl, hydroxyl$C_{1-6}$ alkyl, amino$C_{1-6}$ alkyl, halo$C_{1-6}$ alkyl, $C_{1-6}$ alkoxyl, halo$C_{1-6}$ alkoxyl, $C_{1-6}$ alkoxyl$C_{1-6}$ alkyl, $C_{1-6}$ alkylamino, di($C_{1-6}$ alkyl)amino, di($C_{1-6}$ alkyl)amino$C_{1-6}$ alkyl, $C_{1-6}$ alkylcarbonyl, $C_{1-6}$ alkylcarbonyloxy, $C_{1-6}$ alkoxycarbonyl, carbamyl, carbamyl$C_{1-6}$ alkyl, $C_{1-6}$ alkylcarbamyl, di($C_{1-6}$ alkyl)carbamyl, aminosulfonyl, aminosulfonyl$C_{1-6}$ alkyl, $C_{1-6}$ alkylaminosulfonyl, di($C_{1-6}$ alkyl)aminosulfonyl, $C_{1-6}$ alkylsulfonylamino, alkylsulfonyl, $C_{1-6}$ alkylcarbonylamino or guanidino.

Preferably is:

wherein, $R^1$ is selected from acetylamino, hydroxyl, 1,2,3-triazolyl or isoxazolyloxy;

$R^2$, $R^3$ are independently selected from hydrogen or halogen;

ring A is selected from 5-6 membered cycloalkyl or 5-6 membered heterocyclyl, which are unsubstituted or substituted by 1-2 $R^5$, wherein $R^5$ is independently selected from hydrogen, halogen, $C_{1-4}$ alkyl, halo$C_{1-4}$ alkyl, hydroxyl, hydroxyl$C_{1-4}$ alkyl, amino, $C_{1-4}$ alkylamino, alkyl)amino or $C_{1-4}$ alkylcarbamyl;

ring B is selected from phenyl ring or 5 membered heteroaryl, which are unsubstituted or substituted by 1-2 $R^4$, wherein $R^4$ is independently selected from hydrogen, halogen, $C_{1-4}$ alkyl, halo$C_{1-4}$ alkyl, hydroxyl, hydroxyl$C_{1-4}$ alkyl, amino, $C_{1-4}$ alkyl-amino, di($C_{1-4}$ alkyl)amino or $C_{1-4}$ alkylcarbamyl;

$R^6$ is selected from 5-6 membered heteroaryl containing 1, 2, 3 or 4 N atoms, which is unsubstituted or substituted by 1-2 $R^8$, wherein $R^8$ is selected from $C_{1-4}$ alkyl which is unsubstituted or substituted by halogen.

Preferably is:

wherein, $R^1$ is acetylamino or hydroxyl;

$R^2$, $R^3$ are independently selected from hydrogen or fluoro;

ring A is selected from the following groups, which are unsubstituted or substituted by 1-2 $R^5$: cyclopentyl, cyclohexyl, tetrahydropyrrolyl, 2,3-dihydropyrrolyl, 2,5-dihydropyrrolyl, pyrrolyl, imidazolyl, 4,5-dihydroimidazolyl, pyrazolyl, 4,5-dihydropyrazolyl, 1,2,3-triazolyl, tetrahydrothienyl, thienyl, 2,3-dihydrothienyl, thiazolyl, 4,5-dihydrothiazolyl, isothiazolyl, tetrahydrofuryl, 2,3-dihydrofuryl, furyl, 4,5-dihydrooxazolyl, oxazolyl, 4,5-dihydroisoxazolyl, isoxazolyl, phenyl ring, 1,4,5,6-tetrahydropyrimidinyl, 1,6-dihydropyrimidinyl, 4,5-dihydropyrimidinyl, pyrimidinyl, 3,6-dihydro-2H-pyranyl, 2H-pyranyl, piperidyl, 1,2,3,4-tetrahydropyridyl, 1,2,3,6-tetrahydropyridyl, 2,3-dihydropyridyl, pyridyl, piperazinyl, 1,2,3,4-tetrahydropyrazinyl, 2,3-dihydropyrazinyl or pyrazinyl group, wherein $R^5$ is independently selected from hydrogen, fluoro, methyl, trifluoromethyl, hydroxyl, hydroxylmethyl, amino, methylamino, ethylamino, methylcarbamyl or ethylcarbamyl;

ring B is selected from phenyl ring or 5 membered heteroaryl, which are unsubstituted or substituted by 1-2 $R^4$, wherein $R^4$ is independently selected from hydrogen, fluoro, methyl, fluoromethyl, trifluoromethyl, hydroxyl, hydroxylmethyl, amino, methylamino, ethylamino, methylcarbamyl or ethylcarbamyl;

$R^6$ is selected from the following groups, which are unsubstituted or substituted by 1-2 $R^8$: pyrrolyl, imidazolyl, pyrazolyl, 1,2,3-triazolyl, 1,2,4-triazolyl, 1,2,3,4-tetrazolyl, pyridyl or pyrazinyl, wherein $R^8$ is selected from methyl, ethyl, propyl or trifluoromethyl.

Further preferably is:

wherein, $R^1$ is acetylamino or hydroxyl;

$R^2$, $R^3$ are independently selected from hydrogen or fluoro;

ring A is selected from the following groups, which are unsubstituted or substituted by 1-2 $R^5$: cyclopentyl, cyclohexyl, tetrahydropyrrolyl, 2,3-dihydropyrrolyl, 2,5-dihydropyrrolyl, pyrrolyl, imidazolyl, 4,5-dihydroimidazolyl, pyrazolyl, 4,5-dihydropyrazolyl, 1,2,3-triazolyl, tetrahydrothienyl, thienyl, 2,3-dihydrothienyl, thiazolyl, 4,5-dihydrothiazolyl, isothiazolyl, tetrahydrofuryl, 2,3-dihydrofuryl, furyl, 4,5-dihydrooxazolyl, oxazolyl, 4,5-dihydroisoxazolyl, isoxazolyl, phenyl ring, 1,4,5,6-tetrahydropyrimidinyl, 1,6-dihydropyrimidinyl, 4,5-dihydropyrimidinyl, pyrimidinyl, 3,6-dihydro-2H-pyranyl, 2H-pyranyl, piperidyl, 1,2,3,4-tetrahydropyridyl, 1,2,3,6-tetrahydropyridyl, 2,3-dihydropyridyl, pyridyl, piperazinyl, 1,2,3,4-tetrahydropyrazinyl, 2,3-dihydropyrazinyl or pyrazinyl group, wherein $R^5$ is independently selected from hydrogen, fluoro, methyl, trifluoromethyl, hydroxyl, hydroxylmethyl, amino, methylamino, ethylamino, methylcarbamyl or ethylcarbamyl;

ring B is selected from phenyl ring, thiazolyl, imidazolyl, thienyl, furyl, pyrazolyl, pyrrolyl, 1,2,3-triazolyl, 1,2,4-triazolyl, 1,2,3,4-tetrazolyl, oxazolyl, which are unsubstituted or substituted by 1-2 $R^4$, wherein $R^4$ is independently selected from hydrogen, fluoro, methyl, fluoromethyl, trifluoromethyl, hydroxyl, hydroxylmethyl, amino, methylamino, ethylamino, methylcarbamyl or ethylcarbamyl;

$R^6$ is selected from the following groups, which are unsubstituted or substituted by 1-2 $R^8$: pyrrolyl, imidazolyl, pyrazolyl, 1,2,3-triazolyl, 1,2,4-triazolyl, 1,2,3,4-tetrazolyl, pyridyl or pyrazinyl, wherein $R^8$ is selected from methyl, ethyl, propyl or trifluoromethyl.

Further preferably is:
wherein,
$R^1$ is acetylamino or hydroxyl;
$R^2$, $R^3$ are independently selected from hydrogen or fluoro;
ring A is selected from the following groups, which are unsubstituted or substituted by 1-2 $R^5$: cyclopentyl, cyclohexyl, tetrahydropyrrolyl, 2,3-dihydropyrrolyl, 2,5-dihydropyrrolyl, pyrrolyl, imidazolyl, 4,5-dihydroimidazolyl, pyrazolyl, 4,5-dihydropyrazolyl, 1,2,3-triazolyl, tetrahydrothienyl, thienyl, 2,3-dihydrothienyl, thiazolyl, 4,5-dihydrothiazolyl, tetrahydrofuryl, 2,3-dihydrofuryl, furyl, oxazolyl, phenyl ring, 1,4,5,6-tetrahydropyrimidinyl, 1,6-dihydropyrimidinyl, 4,5-dihydropyrimidinyl, pyrimidinyl, 3,6-dihydro-2H-pyranyl, 2H-pyranyl, piperidyl, 1,2,3,4-tetrahydropyridyl, 1,2,3,6-tetrahydropyridyl, 2,3-dihydropyridyl, pyridyl, piperazinyl, 1,2,3,4-tetrahydropyrazinyl, 2,3-dihydropyrazinyl or pyrazinyl group, wherein $R^5$ is selected from hydrogen, fluoro, methyl or methylcarbamyl;
ring B is selected from phenyl ring, thiazolyl, imidazolyl, thienyl, furyl, pyrazolyl, pyrrolyl, 1,2,3-triazolyl, 1,2,4-triazolyl, oxazolyl, which are unsubstituted or substituted by 1-2 $R^4$, wherein $R^4$ is selected from hydrogen, fluoro, methyl or fluoromethyl;
$R^6$ is selected from 1,2,3-triazolyl, 1,2,4-triazolyl or 1,2,3,4-tetrazolyl, which are unsubstituted or substituted by 1-2 $R^8$, wherein $R^8$ is selected from methyl or ethyl.

SPECIFIC EMBODIMENTS

The "halogen" described by the present invention refers to fluoro atom, chloro atom, bromo atom, iodo atom and the like. Preferred are fluoro atom and chloro atom.

The "halo" described by the present invention refers to that any one of the substitutable atoms in the group is substituted by halogen, which can be perhalo, that is, all possible positions in the group are substituted by halogen atoms.

The "$C_{1-6}$ alkyl" described by the present invention refers to a linear or branched alkyl derived by removing a hydrogen atom from an alkane containing 1-6 carbon atoms. Specific examples include but are not limited to: methyl, ethyl, n-propyl, iso-propyl, n-butyl, 2-methylpropyl, 1-methylpropyl, 1,1-dimethylethyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl and the like. The "$C_{1-4}$ alkyl" described by the present invention refers to specific examples containing 1-4 carbon atoms in the above examples.

The "$C_{2-6}$ alkenyl" described by the present invention refers to a linear or branched or cyclic alkenyl with a number of carbon atoms of 2-6 containing a double bond. Specific examples include but are not limited to: ethenyl, 1-propenyl, 2-propenyl, 3-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,4-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadienyl, 1,4-pentadienyl, 1,4-hexadienyl, cyclopentenyl, 1,3-cyclopentadienyl, cyclohexenyl, 1,4-cyclohexadienyl, 1,3,5-hexatrienyl and the like. The double bond can be optionally cis and trans.

The "$C_{2-6}$ alkynyl" described by the present invention refers to linear or branched alkynyl with a number of carbon atoms of 2-6 containing a triple bond. Specific examples include but are not limited to: ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, 1-ethyl-1-methyl-2-propynyl and the like.

The "C$_{1-6}$ alkoxyl" described by the present invention refers to a group where a "C$_{1-6}$ alkyl" is attached to another structure via an oxygen atom. Specific examples include but are not limited to: methoxy, ethoxy, propoxy, 1-methylethoxy, butoxy, 1-methylpropoxy, 2-methylpropoxy, 1,1-dimethylethoxy, pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexyloxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. The "C$_{1-4}$ alkoxyl" described by the present invention refers to specific examples containing 1-4 carbon atoms in the above examples.

The "C$_{1-6}$ alkylcarbonyl" described by the present invention refers to a group derived by attaching C$_{1-6}$ alkyl to another portion via carbonyl-C(O)—, i.e. C$_{1-6}$ alkyl-C(O)—, wherein the "C$_{1-6}$ alkyl" is as described above. Specific examples include but are not limited to: such as methylcarbonyl, ethylcarbonyl, propylcarbonyl, iso-propylcarbonyl, butylcarbonyl, isobutylcarbonyl, tert-butylcarbonyl, sec-butylcarbonyl, pentylcarbonyl, neopentylcarbonyl, hexylcarbonyl and the like. The "C$_{1-4}$ alkylcarbonyl" described by the present invention refers to specific examples containing 1-4 carbon atoms in the above examples.

The "C$_{1-6}$ alkylcarbonyloxy" described by the present invention refers to a group derived by attaching C$_{1-6}$ alkyl to another portion via carboxyl-C(O)O—, i.e. (C$_{1-6}$ alkyl)C(O)O—, wherein the "C$_{1-6}$ alkyl" is as described above. Specific examples include but are not limited to: methylcarbonyloxy, ethylcarbonyloxy, propylcarbonyloxy, isopropylcarbonyloxy, butylcarbonyloxy, isobutylcarbonyloxy, tert-butylcarbonyloxy, secbutylcarbonyloxy, pentylcarbonyloxy, neopentylcarbonyloxy, hexylcarbonyloxy, and the like.

The "C$_{1-6}$ alkoxycarbonyl" described by the present invention refers to a group derived by attaching C$_{1-6}$ alkoxy to another portion via carbonyl-C(O)—, i.e. (C$_{1-6}$ alkoxy)C(O)—, wherein the "C$_{1-6}$ alkyl" is as described above. Specific examples include but are not limited to: methoxycarbonyl, ethoxycarbonyl, propoxycarbonyl, isopropoxycarbonyl, butoxycarbonyl, isobutoxycarbonyl, tert-butoxycarbonyl, sec-butoxycarbonyl, pentoxycarbonyl, neopentoxycarbonyl, hexyloxycarbonyl, and the like.

The "3-14 membered cycloalkyl" described by the present invention refers to a cyclic group derived by removing a hydrogen atom from an alkane portion of 3-14 carbon atoms, including 3-8 membered monocyclic cycloalkyl, 6-14 membered fused cycloalkyl, 7-12 membered bridge ring group and 7-12 membered spiro ring group. Preferred are C$_{3-8}$ cycloalkyl, C$_{3-6}$ cycloalkyl and C$_{5-6}$ cycloalkyl. The "C$_{3-8}$ cycloalkyl", "C$_{3-6}$ cycloalkyl", "C$_{5-6}$ cycloalkyl", "5-6 membered cycloalkyl" described by the present invention are specific examples below containing 3-8, 3-6, 5-6 carbon atoms, respectively.

The 3-8 membered monocyclic cycloalkyl includes 3-8 membered saturated monocyclic cycloalkyl and 3-8 membered partially saturated monocyclic cycloalkyl. The 3-8 membered saturated monocyclic cycloalkyl refers to a carbocycle wherein the monocyclic ring is completely saturated. Specific examples include but are not limited to: cyclopropyl, cyclobutyl, cyclopentyl, cyclohexyl, cycloheptyl, cyclooctyl, methylcyclopropyl, dimethylcyclopropyl, methylcyclobutyl, dimethylcyclobutyl, methylcyclopentyl, dimethylcyclopentyl, methylcyclohexyl, dimethylcyclohexyl and the like. The 3-8 membered partially saturated monocyclic cycloalkyl refers to a carbocycle wherein the monocyclic ring is partially saturated. Specific examples include but are not limited to cyclopropenyl, cyclobutenyl, cyclopentenyl, cyclohexenyl, 1,4-cyclohexadienyl, cycloheptenyl, 1,4-cycloheptadienyl, cyclooctenyl, 1,5-cyclooctadienyl and the like;

The 6-14 membered fused cycloalkyl refers to a 6-14 membered cyclic group foliated by two or more cyclic structures sharing two adjacent carbon atoms with each other, including 6-14 membered saturated fused cycloalkyl and 6-14 membered partially saturated fused cycloalkyl. Preferred are 6-12 membered fused cycloalkyl, 6-10 membered fused cycloalkyl. The 6-14 membered saturated fused cycloalkyl refers to a carbocycle wherein the fused group is completely saturated. Specific examples include but are not limited to: bicyclo[3.1.0]hexyl, bicyclo[4.1.0]heptyl, bicyclo[2.2.0]hexyl, bicyclo[3.2.0]heptyl, bicyclo[4.2.0]octyl, octahydrocyclopentadienyl, octahydro-1H-indenyl, decahydronaphthyl, tetradecahydrophenanthryl and the like. The 6-14 membered partially saturated fused cycloalkyl refers to a carbocycle wherein at least one of the fused rings is partially saturated. Specific examples include but are not limited to: dicyclo[3.1.0]hex-2-enyl, dicyclo[4.1.0]hept-3-enyl, dicyclo[3.2.0]hept-3-enyl, dicyclo[4.2.0]oct-3-enyl, 1,2,3,3a-tetrahydropentalenyl, 2,3,3a,4,7,7a-hexahydro-1H-indenyl, 1,2,3,4,4a,5,6,8a-octahydronaphthyl, 1,2,4a,5,6,8a-hexahydronaphthyl, 1,2,3,4,5,6,7,8,9,10-decahydrophenanthryl and the like;

The 7-12 membered bridge ring group refers to a structure containing 7-12 carbon atoms formed by any two rings sharing two atoms not connected directly. The "7-12 membered bridge ring" includes 7-12 membered saturated bridge ring group, 7-12 membered partially saturated bridge ring group. Specific examples of the 7-12 membered saturated bridge ring group, preferably 6-10 membered saturated bridge ring group, include but are not limited to: dicyclo[2.1.1]hexyl, dicyclo[2.2.1]heptyl, dicyclo[3.2.0]heptyl, dicyclo[2.2.2]octyl, dicyclo[3.2.1]octyl, dicyclo[3.3.0]octyl, dicyclo[3.3.1]nonyl, dicyclo(4.3.0)nonyl, 4-azadicyclo[5.3.0]decyl and the like. The 7-12 membered partially saturated bridge ring group refers to a cyclic group wherein at least one ring of the bridge ring contains a double bond, preferably a 6-10 membered partially saturated bridge ring group. Specific examples include but are not limited to: dicyclo[2.2.1]hept-5-enyl, dicyclo[3.2.1]oct-6-enyl, dicyclo(4.3.0)non-5-enyl, biscyclopentadienyl and the like;

The 7-12 membered spiro ring group refers to a class of 7-12 membered cyclic structures wherein at least two rings sharing one atom, including 7-12 membered saturated spiro ring group and 7-12 membered partially saturated spiro ring group. The 7-12 membered saturated spiro ring group refers to a cyclic group wherein all rings in the spiro ring group are saturated. Specific examples include but are not limited to: a group formed by substituting any substitutable hydrogen atom of a cyclic structure of

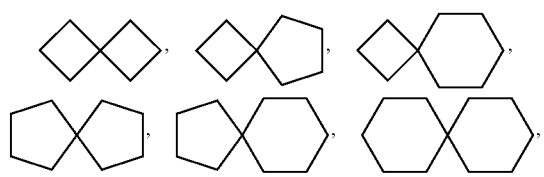

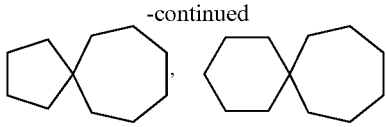

and the like. The 7-12 membered partially saturated spiro ring group refers to a cyclic group wherein at least a ring of the spiro ring group contains a double bond. Specific examples include but are not limited to: a group formed by substituting any substitutable hydrogen atom of a cyclic structure of

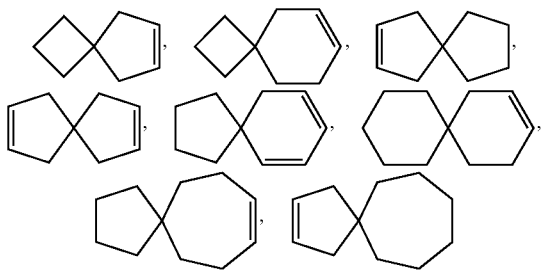

and the like. Preferred are 7-10 membered spiro ring group, including "7-10 membered saturated spiro ring group" and "7-10 membered partially saturated spiro ring group".

The "$C_{3-8}$ cycloalkyloxy" described by the present invention refers to a group wherein the term "$C_{3-8}$ cycloalkyl" is attached to another structure via an oxygen atom. Specific examples include but are not limited to: cyclopropyloxy, cyclobutyloxy, 1-methylcyclobutyloxy, cyclopentyloxy, cyclohexyloxy, cycloheptyloxy, cyclooctyloxy and the like.

The "6-14 membered aryl" described by the present invention refers to a cyclic aromatic group having ring atoms of 6-14 membered carbon atoms, including 6-8 membered monocyclic aryl and 8-14 membered condensed ring aryl. The 6-8 membered monocyclic aryl refers to a completely unsaturated aryl. Specific examples include but are not limited to: phenyl, cyclooctatetraenyl and the like. The 8-14 membered condensed aryl refers to a cyclic group formed by two or more cyclic structures sharing two adjacent carbon atoms with each other, wherein at least one ring is a completely unsaturated aromatic ring, including 8-14 membered completely unsaturated condensed ring aryl. Specific examples include but are not limited to: naphthyl, anthryl and phenanthryl and the like, further including 8-14 membered partially saturated condensed ring aryl, for example, benzo 3-8 membered saturated monocyclic cycloalkyl, benzo 3-8 membered partially saturated monocyclic cycloalkyl. Specific examples include but are not limited to: 2,3-dihydro-1H-indenyl, 1H-indenyl, 1,2,3,4-tetrahydronaphthyl, 1,4-dihydronaphthyl and the like. Preferred are 6-10 membered aryl, and further preferred are phenyl or benzo 3-8 membered saturated monocyclic cycloalkyl, benzo 3-8 membered partially saturated monocyclic cycloalkyl. The term "6-10 membered aryl" refers to specific examples where the number of ring atoms in the above "aryl" is 6-10.

The "5-14 membered heteroaryl" refers to an unsaturated and aromatic cyclic group containing 5-14 ring atoms (wherein containing at least one heteroatom), including 5-8 membered heteroaryl, 6-14 membered condensed heteroaryl. The heteroatoms include nitrogen, oxygen and sulfur and the like, and also include that carbon atom, nitrogen atom and sulfur atom can be replaced by oxygen.

The 5-8 membered heteroaryl refers to an unsaturated and aromatic cyclic group containing 5-8 ring atoms (wherein containing at least one heteroatom selected from nitrogen, oxygen and sulfur), preferably 5-6 membered heteroaryl. Specific examples include but are not limited to furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, 1,4-dioxacyclohexadienyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,2,4-triazinyl, 1,3,5-triazinyl, 1,3,4-triazinyl, 1,2,4,5-tetrazinyl, oxacycloheptantrienyl, thiacycloheptantrienyl, azacycloheptantrienyl, 1,3-diazacycloheptantrienyl, azacyclooctatetraenyl and the like.

The 6-14 membered condensed heteroaryl refers to an unsaturated and aromatic condensed cyclic structure containing 6-14 ring atoms (wherein containing at least one heteroatom) formed by two or more cyclic structures connected by sharing two adjacent atoms with each other. Specific examples include but are not limited to: benzofuryl, benzoisofuryl, benzothienyl, indolyl, benzoxazolyl, benzimidazolyl, indazolyl, benzotriazolyl, quinolyl, isoquinolyl, acridinyl, phenanthridinyl, benzopyridazinyl, phthalazinyl, quinazolinyl, quinoxalinyl, phenazinyl, pteridyl, purinyl, naphthyridinyl and the like. The "5 membered heteroaryl" described by the present invention refers to a heteroaryl containing 5 ring atoms in the above examples. Specific examples include but are not limited to: imidazolyl, furyl, thienyl, pyrrolyl, pyrazolyl, thiazolyl, 1,2,3-triazolyl, 1,2,4-triazolyl, 1,2,3,4-tetrazolyl, 1,2,3,5-tetrazolyl, oxazole, and the like, wherein, preferably pyrazolyl, 1,2,3-triazolyl, 1,2,4-triazolyl, 1,2,3,4-tetrazolyl, 1,2,3,5-tetrazolyl, oxazole and thienyl.

The "3-14 membered heterocyclyl" described by the present invention refers to a 3-14 membered cyclic group containing one to more heteroatoms, including saturated, partially saturated, unsaturated 3-8 membered monoheterocyclyl and 5-14 membered condensed heterocyclyl. The heteroatoms include nitrogen, oxygen and sufure and the like, and also include that carbon atom, nitrogen atom and sulfur atom can be replaced by oxygen. Further included are the above mentioned heteroaryl and dihydro and tetrahydro analogues thereof.

The 5-14 membered condensed heterocyclyl refers to a condensed cyclic group of 5-14 formed by two or more cyclic structures sharing two adjacent atoms with each other, including saturated, partially saturated, unsaturated fused cyclic, spiro ring, bridge rings containing a heteroatom.

The 3-8 membered monoheterocyclyl refers to a monocyclic heterocyclyl containing 3-8 ring atoms (wherein containing at least one heteroatom), including 3-8 membered unsaturated monoheterocyclyl, 3-8 membered partially saturated monoheterocyclyl, 3-8 membered saturated monoheterocyclyl. The 3-8 membered unsaturated monoheterocyclyl refers to an aromatic cyclic group containing a heteroatom. Specific examples include but are not limited to furyl, thienyl, pyrrolyl, thiazolyl, thiadiazolyl, oxazolyl, oxadiazolyl, imidazolyl, pyrazolyl, pyridyl, pyrimidinyl, 1,4-dioxacyclohexadienyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,2,4-triazinyl, 1,3,5-triazinyl, 1,2,4,5-tetrazinyl, oxacycloheptantrienyl, thiacycloheptantrienyl, azacycloheptantrienyl, 1,3-diazacycloheptantrienyl, azacyclooctatetraenyl and the like. The 3-8 membered partially saturated monoheterocyclyl refers to a cyclic group containing a double bond and a heteroatom. Specific examples include but are not limited to 2,5-dihydrothienyl, 4,5-dihydropyrazolyl, 3,4-dihydro-2H-pyranyl, 5,6-dihydro-4H-1,3-oxazinyl and the like. The 3-8 membered saturated monoheterocyclyl refers to a cyclic group containing a heteroatom which is of completely saturated bonds. Specific examples include but are not limited to: azacyclopropyl, azacyclobutyl, thiacyclobutyl, tetrahydrofuryl, tetrahydropyrrolyl, imidazolidinyl, pyrazolidinyl, tetrahydrofuryl, 1,4-dioxacyclohexyl, 1,3-dioxacyclohexyl, 1,3-dithiacyclohexyl, morpholinyl, piperazinyl and the like. Preferred are 5-6 membered heterocyclyl, referring to a group of 5-6 ring atoms in the above examples.

The fused cyclic, spiro ring, bridge ring containing a heteroatoms specifically refers to a 6-14 membered fused heterocyclyl, 5-12 membered spiro heterocyclyl, 5-12 membered bridge heterocyclyl formed by replacing a non common carbon atom in the fused cyclic, spiro ring, bridge ring with a heteroatom.

The 6-14 membered fused heterocyclyl refers to a fused cyclic structure containing 6-14 ring atoms (wherein containing at least one heteroatom) formed by two or more cyclic structures connected by sharing two adjacent atoms with each other, including 6-14 membered unsaturated fused heterocyclyl, 6-14 membered partially saturated fused heterocyclyl, 6-10 membered saturated fused heterocyclyl. The 6-14 membered unsaturated fused heterocyclyl refers to a condensed cyclic structure wherein all rings are unsaturated, such as a structure formed by benzo 3-8 membered unsaturated monoheterocyclyl, a structure formed by 3-8 membered unsaturated monoheterocyclyl fused to 3-8 membered unsaturated monoheterocyclyl and the like. Specific examples include but are not limited to: a group formed by substituting any substitutable hydrogen atom of a cyclic structure of benzofuryl, benzifuryl, benzothienyl, indolyl, benzoxazolyl, benzimidazolyl, indazolyl, benzotriazolyl, quinolyl, isoquinolyl, acridinyl, phenanthridinyl, benzopyridazinyl, phthalazinyl, quinazolinyl, quinoxalinyl, phenazinyl, pteridyl, purinyl, naphthyridinyl,

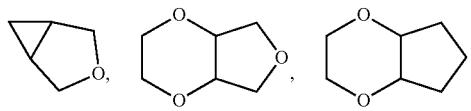

and the like. The 6-14 membered partially saturated fused heterocyclyl refers to a condensed cyclic structure containing at least one partially saturated ring, such as a structure formed by benzo 3-8 membered partially saturated monoheterocyclyl, a structure formed by 3-8 membered partially saturated monoheterocyclyl fused to 3-8 membered partially saturated monoheterocyclyl and the like. Specific examples include but are not limited to: a group formed by substituting any substitutable hydrogen atom of a cyclic structure of 1,3-dihydrobenzofuryl, benzo[d][1.3]dioxolyl, isoindolinyl, chromanyl, 1,2,3,4-tetrahydropyrrolo[3,4-c]pyrrole,

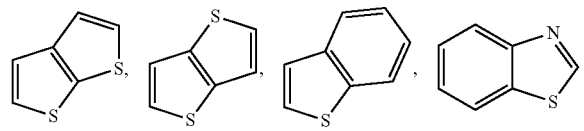

-continued

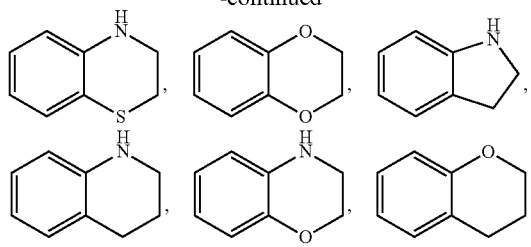

and the like. The 6-10 membered saturated fused heterocyclyl refers to a condensed cyclic structure wherein all rings are saturated, such as a structure formed by 3-8 membered saturated monoheterocyclyl fused to 3-8 membered saturated monoheterocyclyl. Specific examples include but are not limited to: a group formed by substituting any substitutable hydrogen atom of a cyclic structure of cyclobutane fused to tetrahydropyrrolyl, cyclopentane fused to tetrahydropyrrolyl, azetoimidazolidinyl,

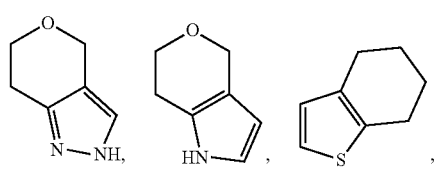

and the like.

The 5-12 membered bridge ring heterocyclyl refers to an bridge ring structure formed by 5-12 ring atoms (wherein containing at least one heteroatom). The "5-12 membered bridge heterocyclyl" includes 5-12 membered saturated bridge heterocyclyl, 5-12 membered partially saturated bridge heterocyclyl.

The 5-12 membered saturated bridge heterocyclyl refers to a cyclic group wherein all rings in the bridge heterocycle are saturated, and preferably is a 7-8 membered saturated bridge heterocyclyl. Specific examples include but are not limited to: a group formed by substituting any substitutable hydrogen atom of a cyclic structure of

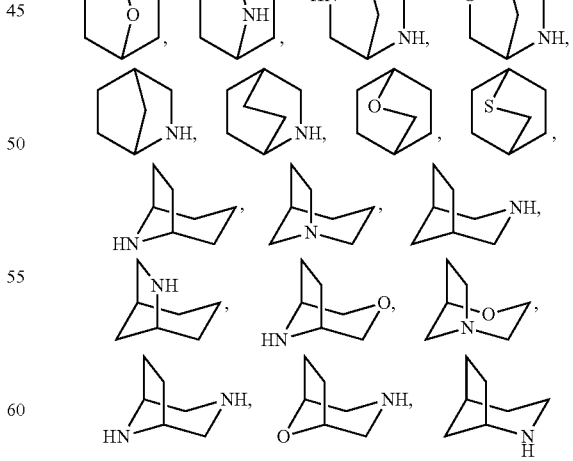

and the like.

The 5-12 membered partially saturated endocyclic heterocyclyl refers to a cyclic group wherein at least one ring of the bridge heterocycle is unsaturated, and preferably is a 7-8 membered partially saturated bridge heterocyclyl. Specific examples include but are not limited to: a group formed by substituting any substitutable hydrogen atom of a cyclic structure of

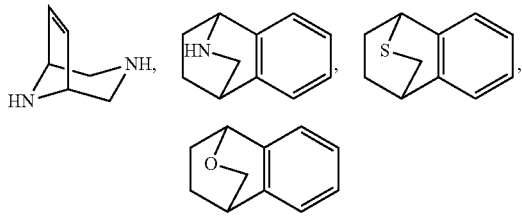

and the like.

The 5-12 membered spiro heterocyclyl refers to a spiro ring structure formed by 5-12 ring atoms (wherein containing at least one heteroatom). The 5-12 membered spiro heterocyclyl includes 5-12 membered saturated spiro heterocyclyl, 5-12 membered partially saturated spiro heterocyclyl.

The 5-12 membered saturated spiro heterocyclyl refers to a cyclic group wherein all the rings in the spiro heterocycle are saturated. Specific examples include but are not limited to: a group formed by substituting any substitutable hydrogen atom of a cyclic structure of

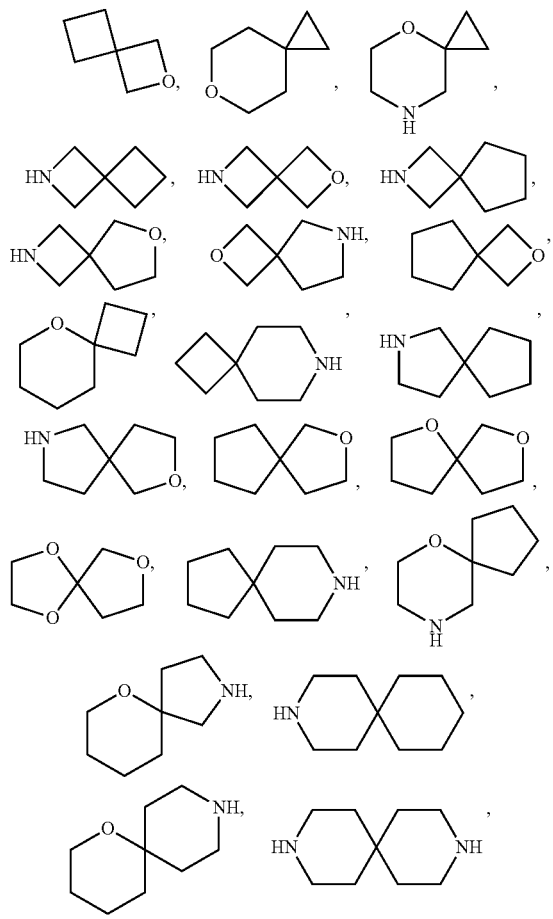

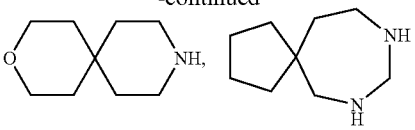

and the like.

The 5-12 membered partially saturated spiro heterocyclyl refers to a cyclic group wherein at least one ring of the spiro heterocycle is unsaturated. Specific examples include but are not limited to: a group formed by substituting any substitutable hydrogen atom of a cyclic structure of

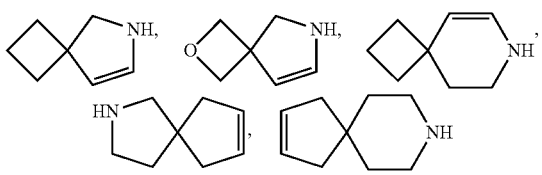

and the like.

The terms 3-8 membered heterocyclyl, 5-7 membered heterocyclyl, 5-6 membered heterocyclyl refer to specific examples wherein the number of ring atoms in the above mentioned "3-14 membered heterocyclyl" is 3-8 membered, 5-8 membered, 5-7 membered, 5-6 membered.

The "3-8 membered cyclic group" described by the present invention refers to a 3-8 membered saturated or unsaturated carbocyclic group or a saturated or unsaturated heterocyclyl group containing a heteroatom, including 3-8 membered saturated carbocyclic group and 3-8 membered unsaturated carbocyclic group, and 3-8 membered saturated heterocyclyl group containing a heteroatom and 3-8 membered unsaturated heterocyclyl group containing a heteroatom. The "5-6 membered cyclic group" described by the present invention refers to specific examples containing 5-6 ring atoms. Wherein:

the "3-8 membered saturated a carbocyclic group" refers to a 3-8 membered cycloalkyl, specific examples include but are not limited to: cyclopropyl, cyclobutyl, cyclopentyl, cyclohexyl, cycloheptyl, cyclooctyl group and the like; wherein, preferred are cyclopropyl, cyclopentyl, cyclohexyl and the like, and more preferred are cyclopentyl, cyclohexyl;

the "3-8 membered unsaturated carbocyclic group" refers to a 3-8 membered cyclic group containing an unsaturated double bond. Specific examples include but are not limited to: cyclopropenyl, cyclobutenyl, cyclopentenyl, cyclohexenyl, cyclopentadienyl, cyclohexadienyl, cycloheptadienyl, cyclooctadienyl group and the like; wherein, preferred are cyclopentenyl, cyclohexenyl, cyclopentadienyl, cyclohexadienyl group and the like; more preferred are cyclopentenyl, cyclopentadienyl;

the "3-8 membered saturated heterocyclyl group containing a heteroatom" refers to a cyclic group containing 3-8 ring atoms (wherein containing at least one heteroatom). Specific examples include but are not limited to: azacyclopropyl, azetidinyl, 1,2-diazetidinyl, pyrrolidinyl, imidazolidinyl, pyrazolidinyl, hydrogenated pyridonyl, piperidyl, piperazinyl, oxiranyl, thiacyclopropyl, oxacyclobutyl, 1,2-dioxacyclobutyl, thiacyclobutyl, tetrahydrofuryl, tetrahydrothienyl, 1,3-dioxacyclopentyl, 1,3-dithiacyclopentyl, tetrahydropyranyl, 1,4-dioxacyclohexyl, 1,3-dioxacyclohexyl, 1,3-oxathiancyclohexyl, oxazolidinyl, morpholinyl group and the like; wherein, preferred are azacyclopropyl, azetidinyl, pyrrolidinyl, imidazolidinyl, pyrazolidinyl, hydrogenated pyridonyl, piperidyl, piperazinyl, oxiranyl, tetrahydrofuryl, tetrahydrothienyl, 1,3-dioxacyclopentyl, 1,3-dithiacyclopentanyl, tetrahydropyranyl, 1,4-dioxacyclohexyl, 1,3-dioxacyclohexyl, 1,3-oxathianyl, oxazolidinyl, morpholinyl group and the like; and the "3-8 membered unsaturated heterocyclyl group containing a heteroatom" refers to a 3-8 (wherein containing at least one heteroatom) heterocyclyl group containing a unsaturated bond in the ring. Specific examples include but are not limited to: azacyclobutadienyl, 1,2-diazacyclobutenyl, pyrrolyl, 4,5-dihydropyrrolyl, 2,5-dihydropyrrolyl, imidazolyl, 4,5-dihydroimidazolyl, pyrazolyl, 4,5-dihydropyrazolyl, 1,2,3-triazolyl, 1,2,4-triazolyl, pyridyl, 2-pyridonyl, 4-pyridonyl, pyridazinyl, pyrimidinyl, pyrazinyl, 1,2,3-triazinyl, 1,2,4-triazinyl, azacycloheptantrienyl, 1,2-diazacycloheptantrienyl, 1,3-diazacycloheptantrienyl, 1,4-diazacycloheptantrienyl, azacyclooctatetraenyl, 1,4-dihydro-1,4-diazacyclooctatrienyl, 1,2-dithiacyclobutenyl, furyl, 4,5-dihydrofuryl, 2,5-dihydrofuryl, thienyl, 2,5-dihydrothienyl, 4,5-dihydrothienyl, 1,2-dithiacyclopentenyl, 1,3-dithiacyclopentenyl, 2H-pyranyl, 2H-pyran-2-one, 3,4-dihydro-2H-pyranyl, 4H-pyranyl, 4H-pyran-4-one, 1,4-dioxacyclohexadienyl, 1,4-dithiacyclohexadienyl, 1,4-oxathiin, oxacycloheptantrienyl, thiacycloheptantrienyl, 1,4-dioxacyclooctatrienyl, oxazolyl, 4,5-dihydrooxazolyl, 2,3-dihydrooxazolyl, isoxazolyl, 4,5-dihydroisoxazolyl, 2,3-dihydroisoxazolyl, 1,2,3-oxadiazolyl, 1,2,5-oxadiazolyl, thiazolyl, 4,5-dihydrothiazolyl, 2,3-dihydrothiazolyl, isothiazolyl, 1,2,3-thiadiazolyl, 2H-1,2-oxazinyl, 4H-1,2-oxazinyl, 6H-1,2-oxazinyl, 2H-1,3-oxazinyl, 4H-1,3-oxazinyl, 5,6-dihydro-4H-1,3-oxazinyl, 6H-1,3-oxazinyl, 2H-1,4-oxazinyl, 4H-1,4-oxazinyl, 2H-1,3-thiazinyl, 4H-1,3-thiazinyl, 5,6-dihydro-4H-1,3-thiazinyl, 6H-1,3-thiazinyl, 2H-1,4-thiazinyl, 4H-1,4-thiazinyl group and the like. Wherein preferred are azacyclobutadienyl, 1,2-diazacyclobutenyl, pyrrolyl, dihydropyrrolyl, imidazolyl, 4,5-dihydroimidazolyl, pyrazolyl, 4,5-dihydropyrazolyl, pyridyl, 2-pyridonyl, 4-pyridonyl, pyridazinyl, pyrimidinyl, pyrazinyl, azacycloheptantrienyl, 1,2-dithiacyclobutenyl, furyl, thienyl, 2,5-dihydrothienyl, 1,2-dithiacyclopentenyl, 2H-pyranyl, 2H-pyran-2-one, 3,4-dihydro-2H-pyranyl, 4H-pyranyl, 4H-pyran-4-one, 1,4-dioxacyclohexadienyl, 1,4-dithiacyclohexadienyl, 1,4-oxathiin, oxacycloheptantrienyl, 1,4-dioxacyclooctatrienyl, oxazolyl, 4,5-dihydrooxazolyl, isoxazolyl, 4,5-dihydroisoxazolyl, 2,3-dihydroisoxazolyl, 1,2,3-oxadiazolyl, 1,2,5-oxadiazolyl, thiazolyl, 4,5-dihydrothiazolyl, isothiazolyl, 1,2,3-thiadiazolyl, 2H-1,2-oxazinyl, 4H-1,2-oxazinyl, 6H-1,2-oxazinyl, 2H-1,3-oxazinyl, 4H-1,3-oxazinyl, 5,6-dihydro-4H-1,3-oxazinyl, 6H-1,3-oxazinyl, 2H-1,4-oxazinyl, 4H-1,4-oxazinyl, 2H-1,3-thiazinyl, 4H-1,3-thiazinyl, 5,6-dihydro-4H-1,3-thiazinyl, 6H-1,3-thiazinyl, 2H-1,4-thiazinyl, 4H-1,4-thiazinyl, morpholinyl, 1,3,4-thiadiazolyl group. More preferred are pyrrolyl, dihydropyrrolyl, imidazolyl, 4,5-dihydroimidazolyl, pyrazolyl, 4,5-dihydropyrazolyl, pyridyl, pyridazinyl, pyrimidinyl, pyrazinyl, furyl, thienyl, 2,5-dihydrothienyl, 2H-pyranyl, 2H-pyran-2-one, 3,4-dihydro-2H-pyranyl, 4H-pyranyl, 4H-pyran-4-one, 1,4-dioxacyclohexadienyl, 1,4-dithiacyclohexadienyl, 1,4-oxathiin, oxazolyl, 4,5-dihydrooxazolyl, isoxazolyl, 4,5-dihydroisoxazolyl, 2,3-dihydroisoxazolyl, 1,2,3-oxadiazolyl, 1,2,5-oxadiazolyl, thiazolyl, 4,5-dihydrothiazolyl, isothiazolyl, 1,2,3-thiadiazolyl, 1,2,4-thiadiazolyl, 1,3,4-thiadiazolyl group and the like.

The "5-6 membered saturated or unsaturated azacyclic group" described by the present invention refers to a cyclic group containing 5-6 ring atoms (wherein containing at least one heteroatom nitrogen) in the above examples. Specific examples include but are not limited to: pyrrolyl, tetrahydropyrrolyl, imidazolidinyl, pyrazolidinyl, imidazolyl, pyrazolyl, 4,5-dihydropyrazole, 1,2,3-triazolyl, 1,2,4-triazolyl, 1,2,3,4-tetrazolyl, 1,2,3,5-tetrazolyl, pyridyl, piperidyl, pyridazinyl, pyrimidinyl, pyrazinyl, piperazinyl, 1,2,3-triazinyl, 1,2,4-triazinyl, 1,3,5-triazinyl, 1,2,4,5-tetrazinyl and the like.

In the compound of general formulas (I) and (II) of the present invention,

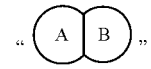

represents a fused condensed bicyclic system formed by ring A and ring B together. Specific examples include but are not limited to: (1) the two atoms shared by ring A and ring B are both carbon atoms; the fused condensed bicyclic system includes, but is not limited to, 2,3-dihydro-1H-indenyl, indolinyl, naphthyl, 1,2,3,4-tetrahydro-quinolyl, 1,2,3,4-tetrahydro-isoquinolyl, isoindolinyl, indolyl, isoindolyl, benzimidazolyl, benzopyrazolyl, benzotriazolyl, 2,3-dihydro-benzothienyl, benzothienyl, benzothiazolyl, 2,3-dihydro-benzofuryl, benzofuryl, benzoxazolyl, 1,2,3,4-tetrahydro-naphthyl, quinolyl, 1,2,3,4-tetrahydro-quinoxalinyl, quinoxalinyl, quinazolinyl, 3,4-dihydro-quinazolinyl, 2H-benzopyranyl, 6,7-dihydro-5H-cyclopentane[b]pyridyl, 3H-imidazole[4,5-b]pyridyl, thiazole[4,5-b]pyridyl, 5,6,7,8-tetrahydro-quinolyl, isoquinolyl and the like, preferably 2,3-dihydro-1H-indenyl, indolinyl, naphthyl, 1,2,3,4-tetrahydro-quinolyl, 1,2,3,4-tetrahydro-isoquinolyl, isoindolinyl and the like. (2) At least one of the two atoms shared by ring A and ring B is a heteroatom, preferably a nitrogen atom. The fused condensed bicyclic system includes, but is not limited to,

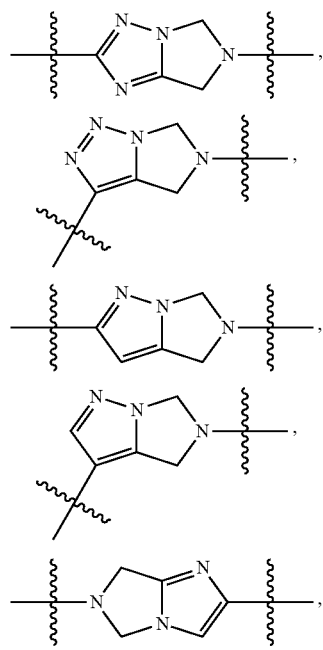

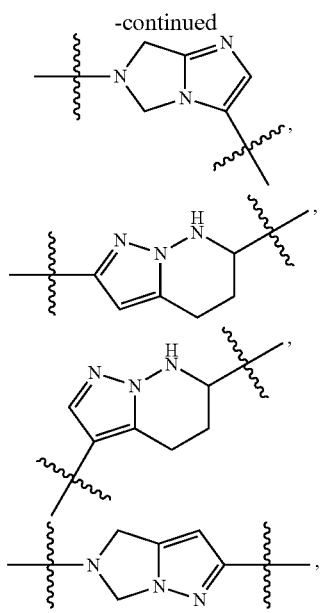

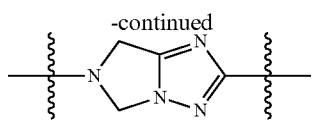

and the like.
Or,

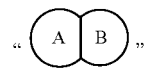

represents a fused condensed bicyclic system formed by ring A and ring B together, including, but not limited to the following circumstances: (1) when ring B is phenyl ring, the two atoms shared by ring A and ring B are both carbon atoms; (2) when ring B is 5 membered heteroaryl, the two atoms shared by ring A and ring B are either both carbon atoms or at least one of the two atoms shared is a heteroatom, preferably a nitrogen atom.

Specifically preferable compounds include:

| Compound | Structural Formula |
|---|---|
| 1 | |
| 2 | |
| 3 | |
| 4 | |

-continued

| Compound | Structural Formula |
|---|---|
| 5 | |
| 6 | |
| 7 | |
| 8 | |
| 9 | |
| 10 | |
| 11 | |
| 12 | |

-continued

| Compound | Structural Formula |
|---|---|
| 13 | |
| 14 | |
| 15 | |
| 16 | |
| 17 | |
| 18 | |
| 19 | |

-continued
| Compound | Structural Formula |
|---|---|
| 20 | 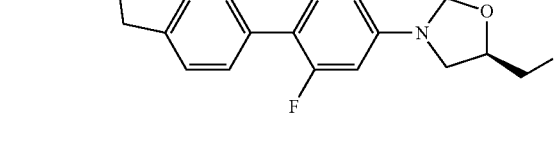 |
| 21 | 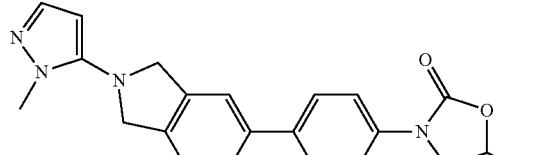 |
| 22 | 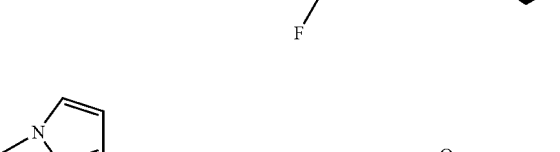 |
| 23 | 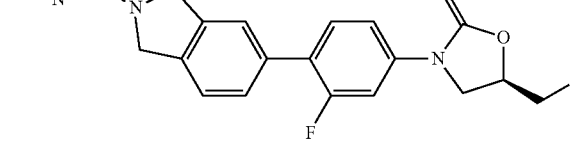 |
| 24 | 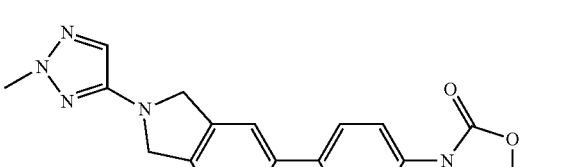 |
| 25 | 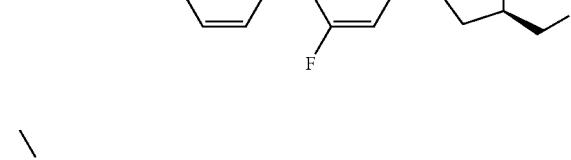 |

-continued

| Compound | Structural Formula |
|---|---|
| 26 | |
| 27 | |
| 28 | |
| 29 | |
| 30 | |

The present invention further provides a method for preparing the above mentioned compounds:

Reaction Equations:

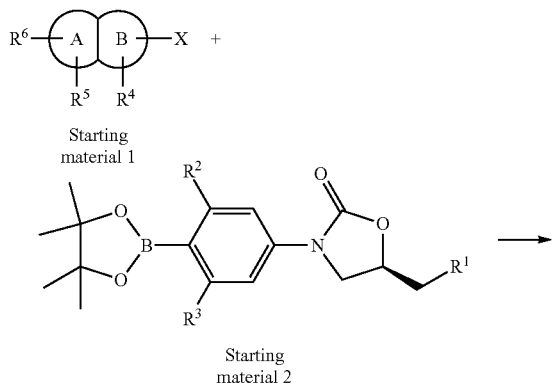

Starting material 1

Starting material 2

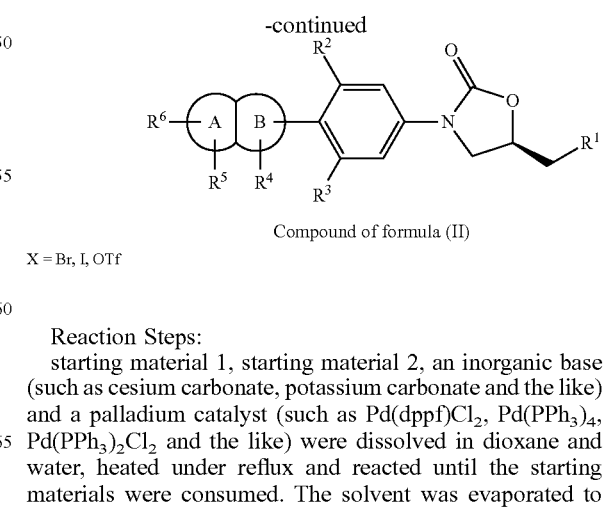

Compound of formula (II)

X = Br, I, OTf

Reaction Steps:

starting material 1, starting material 2, an inorganic base (such as cesium carbonate, potassium carbonate and the like) and a palladium catalyst (such as Pd(dppf)Cl$_2$, Pd(PPh$_3$)$_4$, Pd(PPh$_3$)$_2$Cl$_2$ and the like) were dissolved in dioxane and water, heated under reflux and reacted until the starting materials were consumed. The solvent was evaporated to dryness, and the solid was separated and purified by a silica gel column to obtain compound of formula (II).

Reaction Equations for Another Method:

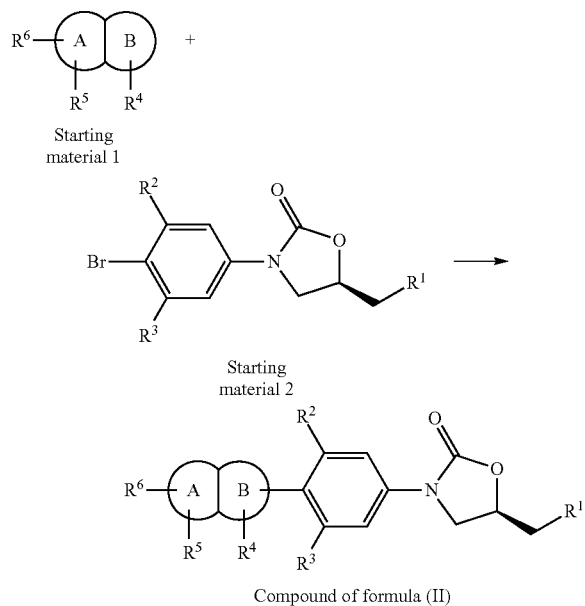

Compound of formula (II)

Reaction Steps:

starting material 1, starting material 2, a base (such as tert-butyl potassium and the like) and a palladium catalyst (such as $Pd_2(dba)_3$, $Pd(dba)_2$ and the like) were dissolved in toluene, heated under reflux and reacted until the starting materials were consumed. The solvent was evaporated to dryness, and the solid was separated and purified by a silica gel column to obtain compound of formula (II).

The starting material 1, starting material 2 in the above reaction equations are both prepared by facile conversion of functional groups of easily accessible starting materials. $R^1$, $R^2$, $R^3$, $R^4$, $R^5$, $R^6$, A or B in the above reaction equations are as defined above.

"A pharmaceutically acceptable salt" of the compound of the present invention refers to a base addition salt or an acid addition salt formed by the compound of the present invention with a pharmaceutically acceptable, non-toxic base or acid, including organic acid salts, inorganic acid salts, organic base salts, and inorganic base salts. Organic acid salts include formate, acetate, propionate, benzene sulfonate, benzoate, p-toluene sulfonate, 2,3-dihydroxylsuccinate, camphor sulfonate, citrate, methane sulfonate, ethane sulfonate, propane sulfonate, fumarate, glyconate, glutamate, hydroxylethane sulfonate, lactate, maleate, malate, mandelate, mucate, bishydroxylnaphthoate, pantothenate, succinate, tartrate and the like. Specifically preferable are benzoate, benzene sulfonate, p-toluene sulfonate, methane sulfonate, citrate, maleate, fumarate, tartrate. Inorganic acid salts include hydrochloride, hydrobromide, hydriodide, sulfate, phosphate, nitrate and the like. Specifically preferable are hydrochloride, hydrobromide, sulfate, phosphate. Organic base salts include amine salts, including salts formed with primary, secondary and tertiary amines, cyclic amine and basic ion exchange resin, which can be selected from salts formed with the following organic bases: for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, meglumine, aminoglucose, histidine, hydrabamine, iso-propylamine, lysine, methylglucosamine, morpholine, piperazine, piperidine, procaine, purine, theobromine, triethylamine, trimethylamine, tripropylamine and tromethamine and the like. Inorganic base salts include salts formed with ammonia, alkali metals, and alkali earth metals, for example, ammonium salt and lithium salt, sodium salt, potassium salt, calcium salt, magnesium salt, zinc salt, barium salt, aluminum salt, ferric salt, cupric salt, ferrous salt, manganese salt, manganous salt. Specifically preferable are ammonium salt and sodium salt, potassium salt, calcium salt, magnesium salt. The compound of formula (I) of the present invention forms phosphate with phosphoric acid, and further forms phosphate metal salt of compound of formula (I) with metal salt, for example, phosphate disodium salt.

"A prodrug" of the compound of the present invention refers to a compound which can be converted to any compound of formula (I) or converted to a pharmaceutically acceptable salt of the compound of formula (I) under physiological condition or via dissolution in solvent (referred as an active drug). When being administered to a patient, the prodrug can be inactive, but it is converted in vivo to an active compound. When hydroxyl is present in the compound of formula (I) of the present invention, an ester-type prodrug can be formed with amino acid, phosphoric acid and the like, and the prodrug is stable in water or acid solution, but dissociates to a free compound under the action of esterase or phosphatase in blood. The prodrug of the compound of formula (I) of the present invention has better solubility than the active drug, is more accessible to be absorbed by an animal or human, and can be converted to an active drug compound better in the blood to exert antibacterial activity.

"Isomers" of the compound of the present invention refers to compounds having the same chemical formula but differ in structure, including conformational isomer (structural isomer) and stereoisomer (configuration isomer) and the like. Structural isomerism includes (carbon) chain isomerism, position isomerism and functional group isomerism (different function isomerism). Stereoisomerism includes conformational and configuration isomerism, and configuration isomerism includes cis-trans isomerism and optical isomerism. "Stereoisomer" refers to that when the compound of the present invention contains one or more asymmetric centers, it can be a racemate and a racemic mixture, a single enantiomer, a diastereomeric mixture and a single diastereomer. The compound of the present invention has asymmetric centers, which independently generate two optical isomers, respectively. The scope of the present invention encompasses all possible optical isomers and diastereomeric mixture and pure or partially pure compounds. If the compound described by the present invention contains an olefinic double bond, the present invention encompasses cis-isomer and trans-isomer, unless specified otherwise.

The compound described by the present invention can present as tautomers, which have different positions of attaching to hydrogen by displacement of one or more double bonds. Each tautomer and mixtures thereof are encompassed by the compound of the present invention.

For example, tautomerism occurs in the compound represented by formula (I) of the present invention and intermediates during preparation thereof, when A representing

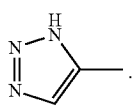

If one of the tautomers is prepared, other tautomers are prepared as well. All the compounds of the present invention and intermediates during preparation involving the above circumstance are regarded equal, and are encompassed within the scope of the present invention.

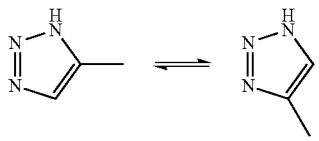

i.e.:

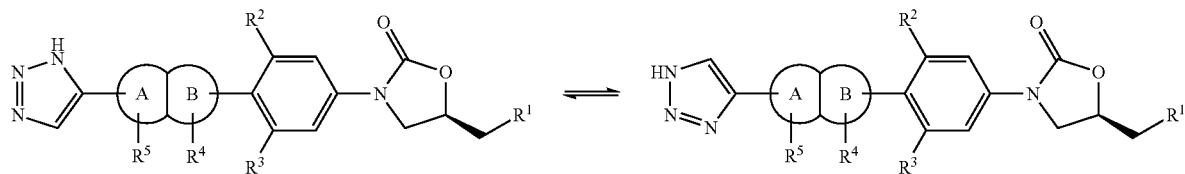

For example, when compound 4 is prepared, it corresponds to the preparation of compound 4'.

Compound 4'

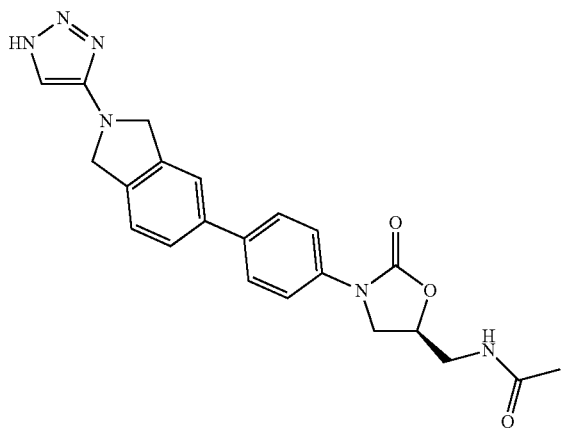

The present invention further provides a pharmaceutical composition comprising the above mentioned compound of general formula (I) of the present invention or a pharmaceutically acceptable salt thereof, an isomer thereof or a prodrug thereof, and one or more a pharmaceutically acceptable carriers and/or diluents. The composition can be made into any clinically or pharmaceutically acceptable dosage form of formulation, preferably oral formulation and injection.

The compounds of the present invention or a pharmaceutically acceptable salt thereof, an isomer thereof or a prodrug thereof can be administered to a mammal, for example human, orally, parenterally (intravenously, intramuscularly, subcutaneously or rectally), topically and the like. The compound of the present invention is used in an amount of about 0.1-100 mg/kg of body weight/day, for example, 3-50 mg/kg of body weight/day.

When being used for parenteral administration, the compound of the present invention or a pharmaceutically acceptable salt thereof, an isomer thereof or a prodrug thereof can be formulated into an injection preparation, including sterile solution, emulsion, dispersion or suspension formulations, and sterile powder or concentrated solution for injection formulated or diluted into solution, dispersion or suspension before use, for intramuscular injection, intravenous injection, intravenous instillation, subcutaneous injection and the like.

The injection preparation can be produced by conventional procedures in the pharmaceutical field, by using aqueous solvents or nonaqueous solvents. The most commonly used aqueous solvent is water for injection, and 0.9% sodium chloride solution or other suitable aqueous solutions can also be used; commonly used nonaqueous solvents are vegetable oil, for example soybean oil for injection, as well as aqueous solutions of ethanol, propylene glycol, polyethylene glycol etc., and the like. The injection preparation can be formulated without adding additives, or suitable additives, such as osmotic modifier, pH modifier, solubilizer, filler, antioxidant, bacteriostat, emulsifier, suspending agent and the like, can be added according to the property of the drug. Commonly used osmotic modifiers include sodium chloride, glucose, potassium chloride, magnesium chloride, calcium chloride, sorbitol and the like, preferably sodium chloride or glucose. Commonly used pH modifiers include acetic acid-sodium acetate, lactic acid, citric acid-sodium citrate, sodium bicarbonate-sodium carbonate and the like. Commonly used solubilizers include Polysorbate 80, propylene glycol, lecithin, polyoxyethylenated castor oil and the like. Commonly used fillers include lactose, mannitol, sorbitol, dextran and the like. Commonly used antioxidants include sodium sulfite, sodium bisulfite, sodium metabisulfite and the like. Commonly used bacteriostats are phenol, cresol, trichloro-tert-butanol and the like.

The pharmaceutical composition can also be formulated to dosage forms for rectal or topical administration, including suppository, ointment, cream, patch, powder, spray, inhalant and the like by conventional methods.

When being used for oral administration, the compound of the present invention or a pharmaceutically acceptable salt thereof, an isomer thereof or a prodrug thereof can be formulated by conventional methods into conventional solid formulations, such as tablet, capsule, pill, granule and the like; and can be formulated into oral liquid formulations, such as oral solution, oral suspension, syrup and the like. Tablets are predominantly oral compressed tablets, and include buccal tablet, sublingual tablet, buccal patch, chewable tablet, dispersible tablet, soluble tablet, effervescent tablet, sustained release tablet, controlled release tablet and enteric coated tablet and the like. Based on the solubility and release properties thereof, capsules can be divided into hard capsule, soft capsule, sustained release capsule, controlled release capsule and enteric coated capsule and the like. Pills include dripping pill, rotula, parvule and the like. Granules can be divided into soluble granule, suspensible granule, effervescent granule, enteric coated granule, sustained release granule and controlled release granule and the like.

In the preparation of oral formulation, suitable filler, binder, disintegrant, lubricant and the like can be added. Commonly used fillers include starch, powdered sugar, calcium phosphate, calcium sulfate dihydrate, dextrin, microcrystalline cellulose, lactose, pregelatinized starch, mannitol and the like. Commonly used binders include sodium carboxymethyl cellulose, PVP-K30, sodium hydroxypropyl cellulose, starch slurry, methyl cellulose, ethyl cellulose, hydroxypropyl methylcellulose, gelatinized starch and the like. Commonly used disintegrants include dry starch, crospovidone, crosslinked sodium carboxymethyl cellulose, sodium carboxymethyl starch, low-substituted hydroxypropyl cellulose and the like. Commonly used lubricants include magnesium stearate, talc powder, sodium dodecylsulfate, micronized silica gel and the like.

In another aspect, the present invention further provides a use of the compound of general formula (I) of the present invention or a pharmaceutically acceptable salt thereof, an isomer thereof or a prodrug thereof for the manufacture of a medicament for the treatment and/or prevention of infectious diseases.

In yet another aspect, the present invention further provides a method for treating and/or preventing infectious diseases, which comprises administering the compound of general formula (I) of the present invention or a pharmaceutically acceptable salt thereof, an isomer thereof or a prodrug thereof to a mammal, for example human in need of the treatment or prevention.

Tests prove that the compounds of the present invention have good antibacterial activity, and can be used for the treatment and/or prevention of various infectious diseases.

The oxazolidinones antibacterials of the present invention have good antibacterial activity against Gram-positive bacteria, as well as good antibacterial activity against drug resistant Gram-positive bacteria, and can be used for the treatment and/or prevention of various diseases induced by Gram-positive bacteria.

The beneficial effects of the compounds of the present invention are further illustrated by antibacterial activity assays. However, it should not be interpreted as the compounds of the present invention only have the following beneficial effects.

EXAMPLE

The In Vitro Antibacterial Activity of the Compounds of the Present Invention

Strains for test: all the clinically separated strains below were purchased from public facilities.

Methicillin-resistant *Staphylococcus aureus* (MRSA), methicillin-resistant *Staphylococcus epidermidis* (MRSE), methicillin-sensitive *Staphylococcus aureus* (MSSA), methicillin-sensitive *Staphylococcus epidermidis* (MSSE), *Enterococcus faecalis* (efa), *Enterococcus faecium* (efm), *streptococcus pneumoniae*. Obtained from: Qianfoshan Hospital, First People's Hospital of Yunnan Province, Renji Hospital of Shanghai, People's Hospital of Jilin Province, Southwest Hospital.

Test Compounds:

some compounds of the present invention (chemical names and preparation methods thereof are as described in Preparation Examples of the compounds); linezolid (commercially available) and compound 38 (prepared following the process of Patent US2011098471).

Test Method:

standard agar dilution method, reference was made to National Committee for Clinical Laboratory Standards. 2006. Methods for Dilution Antimicrobial Susceptibility Tests for Bacteria That Grow Aerobically, Approved Standard Seventh Edition M7-A7.

Test Results and Conclusion:

TABLE 1

The antibacterial activity of the compounds of the present invention

| | Antibiotic Activity MIC (µg/mL) | | | | | | |
|---|---|---|---|---|---|---|---|
| Compound | MRSA | MRSE | MSSA | MSSE | efa | efm | Streptococcus pneumoniae |
| Linezolid | 2 | 1 | 2 | 2 | 2 | 2 | 2 |
| Compound 38 | 0.5 | 0.25 | 0.5 | 0.5 | 0.25 | 0.5 | 0.5 |
| 1 | 1 | 0.5 | 1 | 0.5 | 1 | 0.5 | 0.25 |
| 2 | 0.25 | 0.25 | 0.5 | 0.5 | 0.5 | 0.5 | 0.5 |
| 3 | 0.5 | 0.25 | 0.5 | 0.125 | 0.5 | 0.5 | 0.5 |
| 4 | 0.25 | 0.25 | 0.25 | 0.125 | 0.25 | 0.25 | 0.5 |
| 19 | 1 | 1 | 1 | 0.5 | 2 | 2 | 1 |
| 20 | 2 | 0.5 | 1 | 0.5 | 8 | 8 | — |

Symbol "—" represent that the antibiotic activity of the strain is not investigated.

It can be seen from the above test results that the compounds of the present invention all have higher antibacterial activity to the strains for test. Some compounds have better antibiotic activity than the medication in the market. Compared with the control group of compound 38, the antibiotic activity is comparable or higher. The compounds of the present invention have better clinical potence.

4. Specific Embodiments

The above content of the present invention is further illustrated in detail by the specific embodiments as examples below. However, it should not be interpreted as that the scope of the above subjects of the present invention is only limited to the examples below. Any technology achieved based on the above content of the present invention is encompassed by the present invention.

Example 1

Preparation of (R)-3-(3-fluoro-4-(2-(2-methyl-2H-tetrazol-5-yl) isoindolin-5-yl)phenyl)-5-(hydroxylmethyl)oxazolidin-2-one (Compound 1)

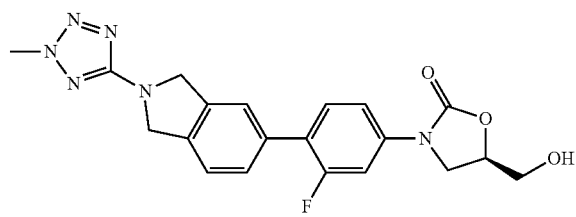 [SMILES: Cn1nnc(N2Cc3ccc(-c4ccc(N5C[C@H](CO)OC5=O)cc4F)cc3C2)n1]

(1) Preparation of 5-bromoisoindolin-2-carbonitrile

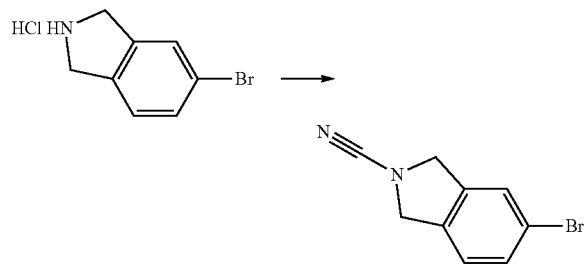

5-Bromoisoindoline (20 g, 85.28 mmol) and triethylamine (21.6 mL, 154.97 mmol) were dissolved in 250 mL dichloromethane, and bromoacetonitrile (9.03 g, 85.3 mmol) was added slowly. The mixture was stirred at room temperature and reacted for 4 h. Water was added. After being extracted with ethyl acetate, dried, and concentrated, 5-bromo isoindolin-2-carbonitrile (14 g) was obtained at a yield of 73.6%. The solid was used directly for the next step of reaction without purification.

(2) Preparation of 5-bromo-2-(2H-tetrazol-5-yl)isoindoline

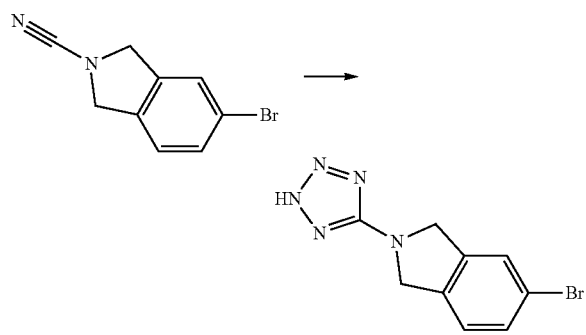

5-Bromoisoindoline-2-carbonitrile (14 g, 62.8 mmol) was dissolved in 100 mL DMF, and then sodium azide (4.9 g, 75.4 mmol) and ammonium chloride (6.71 g, 124.7 mmol) were added. The reaction solution was heated to 110° C. and reacted for 10 h, and then cooled to room temperature. The reaction solution was used directly for the next step of reaction without treatment.

(3) Preparation of 5-bromo-2-(2-methyl-2H-tetrazol-5-yl)isoindoline

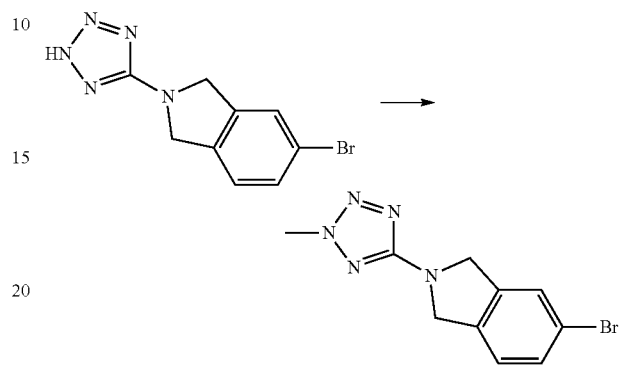

NaOH (2.51 g, 62.8 mmol) was added into the above reaction solution, and then iodomethane (8.91 g, 62.8 mmol) was added dropwise. After being reacted for 10 h at room temperature, the solvent was evaporated to dryness, and the residual solid was separated by a silica gel column (petroleum ether:ethyl acetate=4:1) to obtain 1.7 g of 5-bromo-2-(2-methyl-2H-tetrazol-5-yl)isoindoline, at an overall yield over two steps of reactions of 9.7%.

(4) Preparation of (R)-3-(4-bromo-3-fluorophenyl)-5-(hydroxylmethyl)oxazolidin-2-one

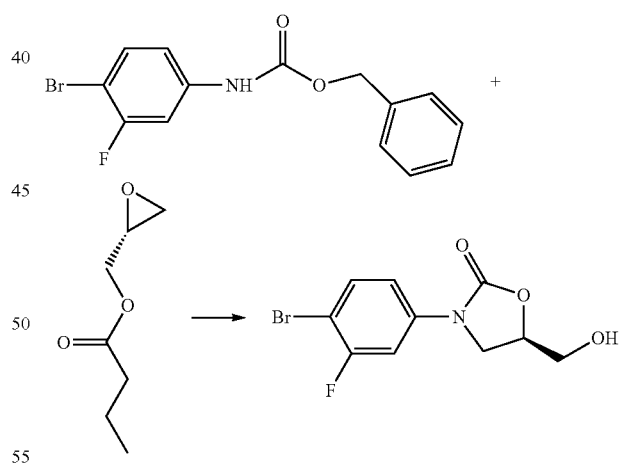

Benzyl 4-bromo-3-fluorophenylcarbamate (20 g, 61.7 mmol) was dissolved in 180 mL THF, cooled to −78° C., and LiHMDS (1.0M in THY, 62.4 mL, 62.4 mmol) was added dropwise within 45 min. After continued to stir for 30 min, R-glycidyl butyrate (2.21 mL, 62.3 mmol) was added dropwise. After continued to react for 1 h at low temperature, it was warmed to room temperature and reacted for 60 h. The reaction was quenched with saturated ammonium chloride. Water was added, and extracted with ethyl acetate. The organic phase was dried, concentrated, and then separated by a silica gel column (petroleum ether:ethyl acetate=2:1) to obtain 8.1 g of (R)-3-(4-bromo-3-fluorophenyl)-5-(hydroxylmethyl)oxazolidin-2-one, at a yield of 45.3%.

(5) Preparation of (R)-3-(3-fluoro-4-(4,4,5,5-tetramethyl-1,3,2-dioxaborolan-2-yl)phenyl)-5-(hydroxylmethyl)oxazolidin-2-one

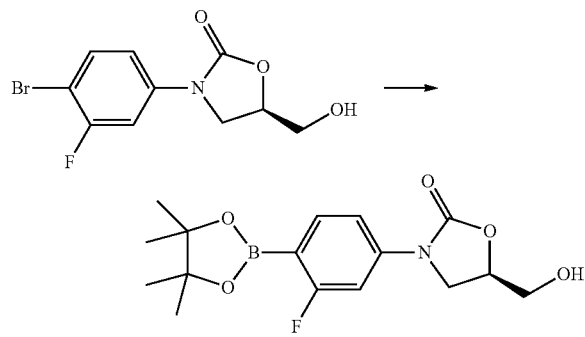

(R)-3-(4-bromo-3-fluorophenyl)-5-(hydroxylmethyl)oxazolidin-2-one (7 g, 24.1 mmol) was dissolved in 120 mL dioxane, and bis(pinacolato)diboron (7.38 g, 29 mmol), potassium acetate (2.45 g, 25 mmol) and Pd(Ph₃P)₂Cl₂ (0.7 g, 0.1 mmol) were added. It was heated to 90° C. and reacted overnight. Water was added, extracted with ethyl acetate, dried, concentrated, and then separated by a silica gel column (petroleum ether:ethyl acetate=1:1) to obtain 5 g of (R)-3-(3-fluoro-4-(4,4,5,5-tetramethyl-1,3,2-dioxaborolan-2-yl)phenyl)-5-(hydroxylmethyl)oxazolidin-2-one, at a yield of 61.5%.

(6) Preparation of (R)-3-(3-fluoro-4-(2-(2-methyl-2H-tetrazol-5-yl)isoindolin-5-yl)phenyl)-5-(hydroxylmethyl)oxazolidin-2-one

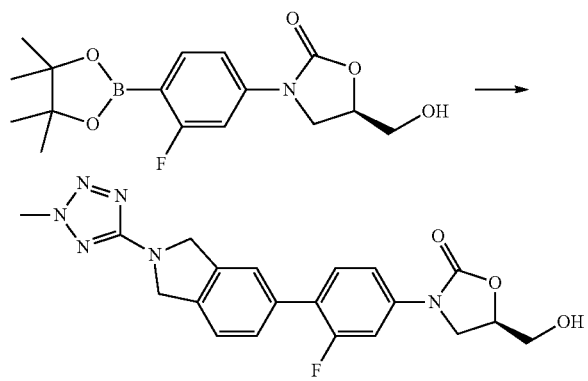

5-Bromo-2-(2-methyl-2H-tetrazol-5-yl)isoindoline (500 mg, 1.78 mmol), (R)-3-(3-fluoro-4-(4,4,5,5-tetramethyl-1,3,2-dioxaborolan-2-yl)phenyl)-5-(hydroxylmethyl) oxazolidin-2-one (600 mg, 1.78 mmol), cesium carbonate (580 mg, 1.78 mmol) and Pd(dppt)Cl₂ (100 mg, 0.14 mmol) were dissolved in 50 mL dioxane and 1 mL water, heated to 100° C. and reacted for 3 h. The solvent was evaporated to dryness, and the solid was separated by a silica gel column (dichloromethane:methanol=50:1) to obtain 225 mg of (R)-3-(3-fluoro-4-(2-(2-methyl-2H-tetrazol-5-yl)isoindolin-5-yl)phenyl)-5-(hydroxylmethyl) oxazolidin-2-one, at a yield of 31%.

Molecular formula: $C_{20}H_{19}FN_6O_3$ Molecular weight: 410.4 Mass spectrum (m/e): 411.2 (M+H)

$^1$H-NMR (400 MHz, DMSO-d₆) δ: 7.64-7.42 (m, 6H), 5.24 (t, 1H), 4.74 (s, 4H), 4.75 (m, 1H), 4.20 (s, 3H), 4.12 (t, 1H), 3.87 (m, 1H), 3.64 (m, 1H), 3.57 (m, 1H).

Example 2

Preparation of (S)—N-((3-(3-fluoro-4-(2-(2-methyl-2H-tetrazol-5-yl) isoindolin-5-yl)phenyl)-2-oxo-oxazolidin-5-yl)methyl)acetamide (Compound 2)

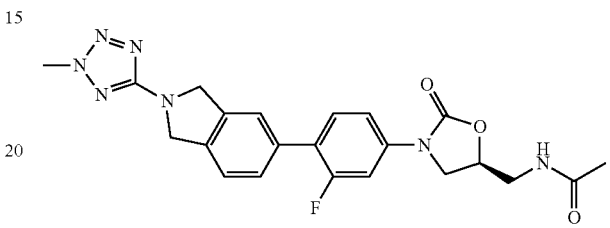

(1) Preparation of (5S)—N-[[3-[3-fluoro-4-(4,4,5,5-tetramethyl-1,3,2-dioxaborolan-2-yl) phenyl]-2-oxo-oxazolidin-5-yl]methyl]acetamide

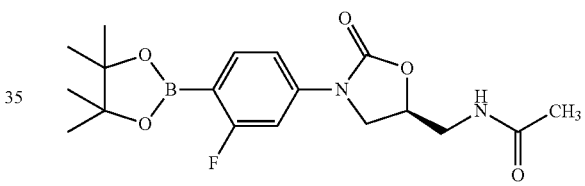

Into a dry reaction flask were added 30 mL 1,4-dioxane, 3.31 g (10 mmol) (5S)—N-[[3-(3-fluoro-4-bromophenyl)-2-oxo-oxazolidin-5-yl]methyl]acetamide, 2.54 g (10 mmol) bis(pinacolato)diborolane, and 0.98 g (10 mmol) potassium acetate, and argon gas was introduced into the flask. And then 0.3 g Pd(PPh₃)₂Cl₂ was added, continued to introduce argon gas into the reaction solution, stirred at 90° C. and reacted overnight. The resulted reaction mixture was cooled to room temperature, and filtered through diatomite, extracted with ethyl acetate and saline. The organic layer was dried over anhydrous sodium sulfate, and concentrated. A grey solid precipitated, and was filtered to obtain 3.22 g of product, at a yield of 85.2%.

(2) Preparation of (S)—N-((3-(3-fluoro-4-(2-(2-methyl-2H-tetrazol-5-yl)isoindolin-5-yl)phenyl)-2-oxo-oxazolidin-5-yl)methyl)acetamide

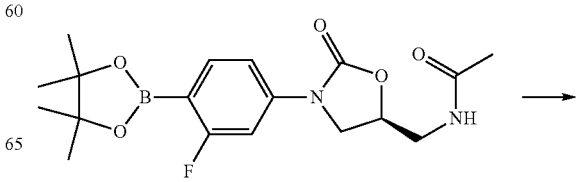

-continued

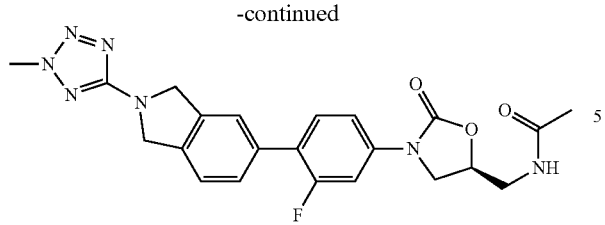

The procedure was the same as Example 1 (6), at a yield of 16.8%.

Molecular formula: $C_{22}H_{22}FN_7O_3$ Molecular weight: 451.4 Mass spectrum (m/e): 452.2 (M+H).

$^1$H-NMR (400 MHz, DMSO-$d_6$) δ: 8.25 (t, 1H), 7.59-7.61 (m, 3H), 7.55 (s, 2H), 7.40 (d, 1H), 4.77 (s, 4H), 4.76 (m, 1H), 4.18 (m, 4H), 3.42 (t, 3H), 1.83 (s, 3H).

Example 3

Preparation of (R)-3-(4-(2-(1H-1,2,3-triazol-5-yl)isoindolin-5-yl)-3-fluorophenyl)-5-(hydroxylmethyl)oxazolidin-2-one (Compound 3)

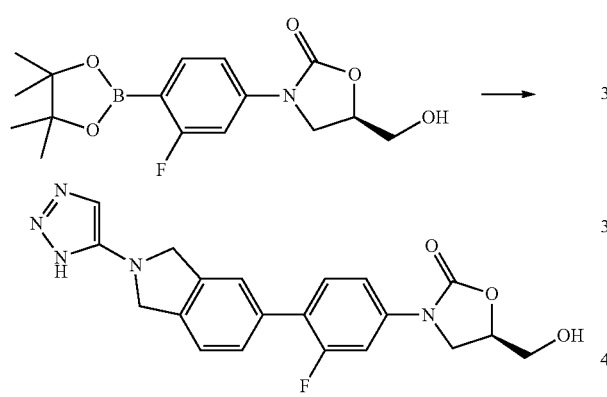

The procedure was the same as Example 1 (6), at a yield of 8%.

Molecular formula: $C_{20}H_{18}FN_5O_3$ Molecular weight: 395.4 Mass spectrum (m/e): 396.2 (M+H)

$^1$H-NMR (400 MHz, DMSO-$d_6$) δ: 13.93 (br s, 1H), 7.60-7.64 (m, 3H), 7.56 (m, 3H), 7.22 (s, 1H), 5.25 (t, 1H), 4.74 (s, 1H), 4.60 (m, 4H), 4.14 (t, 1H), 3.88 (t, 1H), 3.70 (m, 1H), 3.58 (m, 1H).

Example 4

Preparation of (S)—N-((3-(4-(2-(1H-1,2,3-triazol-5-yl)isoindolin-5-yl)-3-fluorophenyl)-2-oxo-oxazolidin-5-yl)methyl)acetamide (Compound 4)

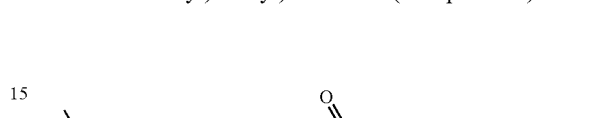

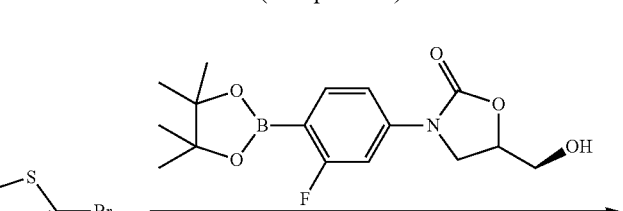

The procedure was the same as Example 2, at a yield of 16%.

Molecular formula: $C_{22}H_{21}FN_6O_3$ Molecular weight: 436.4 Mass spectrum (m/e): 437.2 (M+H)

$^1$H-NMR (400 MHz, DMSO-$d_6$) δ: 13.92 (s, 1H), 8.26 (s, 1H), 7.61-7.40 (m, 6H), 7.22 (s, 1H), 4.74 (s, 1H), 4.60 (m, 4H), 4.16 (t, 1H), 3.78 (t, 1H), 3.42 (m, 2H), 1.83 (s, 3H).

Example 5

Preparation of (R)-3-(3-fluoro-4-(5-(2-methyl-2H-tetrazol-5-yl)-5,6-dihydro-4H-pyrrolo[3,4-d]thiazol-2-yl) phenyl)-5-(hydroxylmethyl)oxazolidin-2-one (Compound 5)

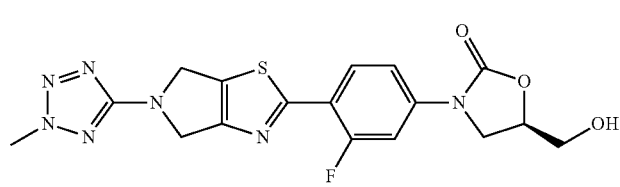

The procedure was the same as Example 1 (6), at a yield of 9.3%.

Molecular formula: $C_{17}H_{16}FN_7O_3S$ Molecular weight: 417.4 Mass spectrum (m/e): 418.2 (M+H)

$^1$H-NMR (400 MHz, DMSO-d$_6$) δ: 8.21 (t, 1H), 7.71 (d, 1H), 7.54 (d, 1H), 5.25 (t, 1H), 4.81 (s, 2H), 4.75 (m, 1H), 4.69 (s, 2H), 4.20 (s, 3H), 4.14 (t, 1H), 3.89 (m, 1H), 3.67 (m, 1H), 3.58 (m, 1H).

Example 6

Preparation of (R)-(3-(3-fluoro-4-(5-(2-methyl-2H-tetrazol-5-yl)-5,6-dihydropyrrolo[3,4-c]pyrazol-2(4H)-yl)phenyl)-5-(hydroxylmethyl)oxazolidin-2-one (Compound 12)

(1) 2-(2-fluoro-4-nitrophenyl)-5-(2H-tetrazol-5-yl)-2,4,5,6-tetrahydropyrrolo[3,4-c]pyrazole

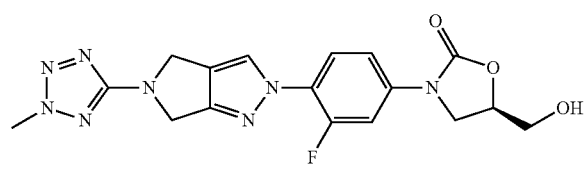 [SMILES: Cn1nnc(N2Cc3cn(-c4ccc(N5C[C@H](CO)OC5=O)cc4F)nc3C2)n1]

2-(2-fluoro-4-nitrophenyl)-4,6-dihydropyrrolo[3,4-c]pyrazol-5 (2H)-acetonitrile (4.2 g, 15.4 mmol) was dissolved in 50 mL DMF, and then sodium azide (2.57 g, 39.5 mmol) and ammonium chloride (3.98 g, 132.4 mmol) were added. The reaction solution was heated to 110° C. and reacted for 10 h, and then cooled to room temperature. The reaction solution was used directly for the next step of reaction without treatment.

(2) 2-(2-fluoro-4-nitrophenyl)-5-(2-methyl-2H-tetrazol-5-yl)-2,4,5,6-tetrahydropyrrolo [3,4-c]pyrazole

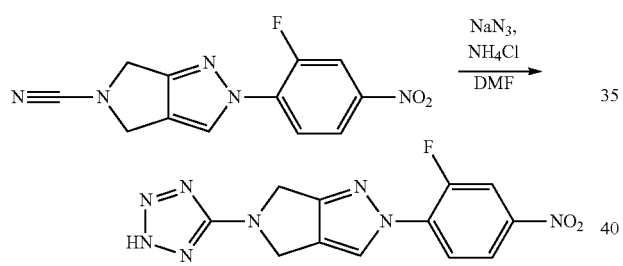

NaOH (8.0 g, 20 mmol) was added into the above reaction solution, and then 20 mL iodomethane was added dropwise. After reacted for 18 h at room temperature, the solvent was evaporated to dryness. The residual solid was used directly for the next step of reaction without purification.

(3) 3-fluoro-4-(5-(2-methyl-2H-tetrazol-5-yl)-5,6-dihydropyrrolo[3,4-c]pyrazol-2(4H)-yl) phenyl amine

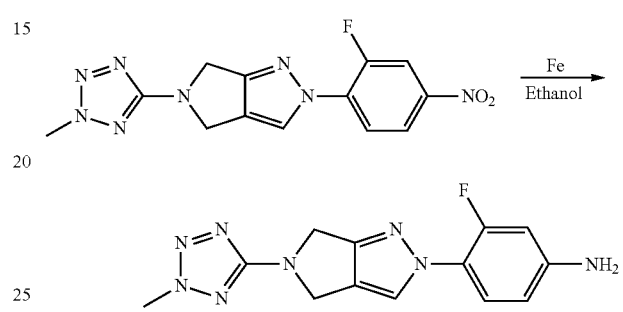

2-(2-Fluoro-4-nitrophenyl)-5-(2-methyl-2H-tetrazol-5-yl)-2,4,5,6-tetrahydropyrrolo[3,4-c]pyrazole (1.2 g, 3.6 mmol) was dissolved in a mixture of 10 mL ethanol and 1 mL hydrochloric acid, and iron powder (340 mg, 6.1 mmol) was added. It was heated to 80° C. and reacted for 0.5 hr. After filtration, a solid was obtained by concentrating. The solid was used directly for the next step of reaction without purification.

(4) Benzyl 3-fluoro-4-(5-(2-methyl-2H-tetrazol-5-yl)-5,6-dihydropyrrolo[3,4-c]pyrazol-2(4H)-yl)phenylcarbamate

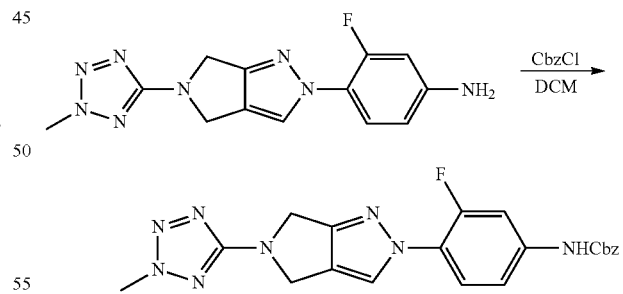

The solid from the last step was dissolved in 30 mL dichloromethane, and 2 mL triethylamine and 1.5 mL CbzCl were added. After stirred and reacted for 2 h at room temperature, water was added and the layers were separated. The organic layer was dried. The concentrated solid was separated by a silica gel column (methanol:dichloromethane=50:1) to obtain 1.2 g of benzyl 3-fluoro-4-(5-(2-methyl-2H-tetrazol-5-yl)-5,6-dihydropyrrolo[3,4-c]pyrazol-2(4H)-yl)phenylcarbamate, at a yield of 77%.

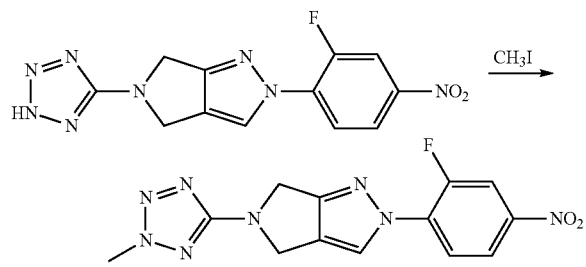

(5) Preparation of (R)-(3-(3-fluoro-4-(5-(2-methyl-2H-tetrazol-5-yl)-5,6-dihydropyrrolo [3,4-c]pyrazol-2 (4H)-yl)phenyl)-5-(hydroxylmethyl)oxazolidin-2-one

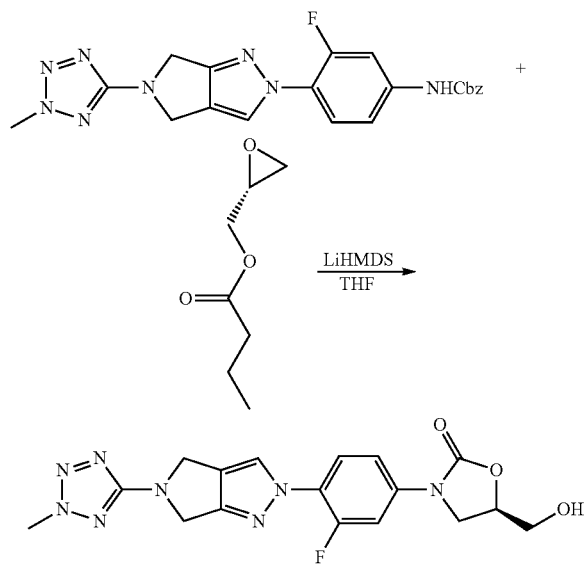

Benzyl 3-fluoro-4-(5-(2-methyl-2H-tetrazol-5-yl)-5,6-dihydropyrrolo[3,4-c]pyrazol-2 (4H)-yl)phenylcarbamate (1.2 g, 2.76 mmol) was dissolved in 25 mL THF, cooled to −78° C., and LiHMDS (1.0 M in THF, 13.8 mL, 13.8 mmol) was added dropwise within 45 min. After continued to stir for 30 min, R-glycidyl butyrate (2.0 g, 13.9 mmol) was added dropwise. After continued to react for 1 h at a low temperature, it was warmed to room temperature and reacted for 60 h. The reaction was quenched with saturated ammonium chloride. Water was added, and extracted with ethyl acetate. The organic phase was dried, concentrated, and then separated by a silica gel column (dichloromethane:methanol=10:1) to obtain 110 mg of (R)-(3-(3-fluoro-4-(5-(2-methyl-2H-tetrazol-5-yl)-5,6-dihydropyrrolo[3,4-c]pyrazol-2 (4H)-yl)phenyl)-5-(hydroxylmethyl)oxazolidin-2-one, at a yield of 10%.

Molecular formula: $C_{17}H_{17}FN_8O_3$ Molecular weight: 400.4 Mass spectrum (m/e): 401.1 (M+H)

$^1$H-NMR (400 MHz, DMSO-$d_6$) δ: 7.75 (m, 2H), 7.68 (s, 1H), 7.51 (d, 1H), 5.26 (t, 1H), 4.75 (m, 1H), 4.67 (s, 2H), 4.54 (s, 2H), 4.18 (s, 3H), 4.13 (t, 1H), 3.88 (m, 1H), 3.67 (m, 1H), 3.58 (m, 1H).

Example 7

Preparation of (R)-(3-(3-fluoro-4-(5-(2-methyl-2H-tetrazol-5-yl)-5,6-dihydropyrrolo[3,4-d][1,2,3]-triazol-2(4H)-yl)phenyl)-5-(hydroxylmethyl)oxazolidin-2-one (Compound 13)

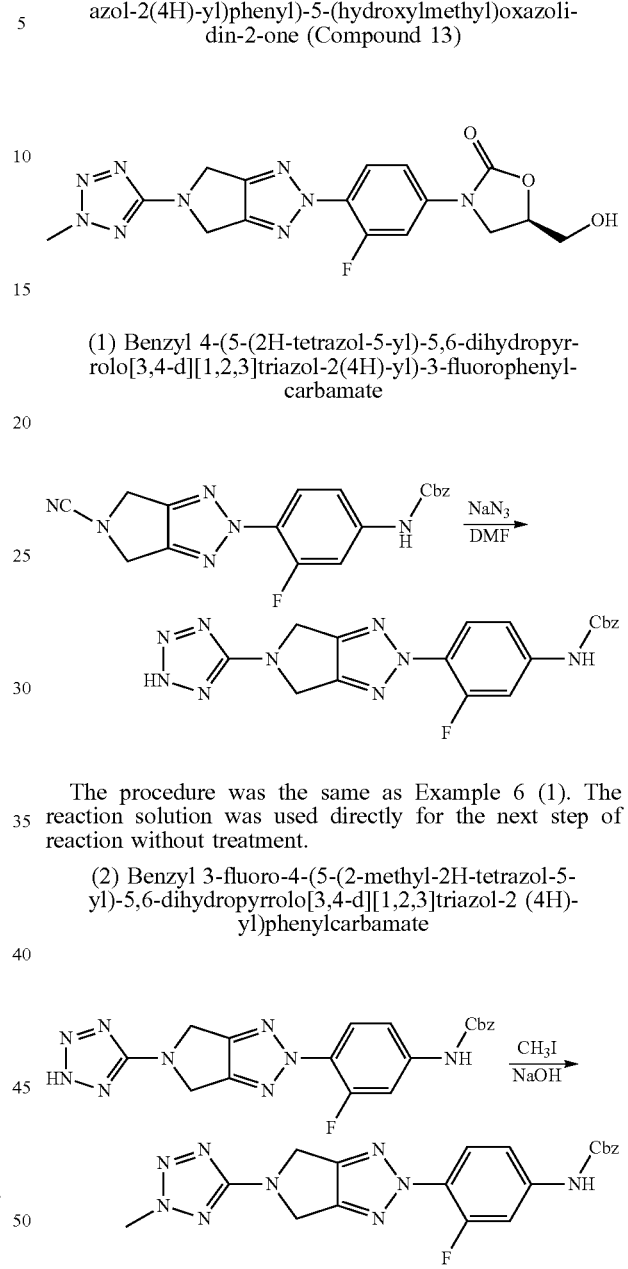

(1) Benzyl 4-(5-(2H-tetrazol-5-yl)-5,6-dihydropyrrolo[3,4-d][1,2,3]triazol-2(4H)-yl)-3-fluorophenylcarbamate The procedure was the same as Example 6 (1). The reaction solution was used directly for the next step of reaction without treatment.

(2) Benzyl 3-fluoro-4-(5-(2-methyl-2H-tetrazol-5-yl)-5,6-dihydropyrrolo[3,4-d][1,2,3]triazol-2 (4H)-yl)phenylcarbamate

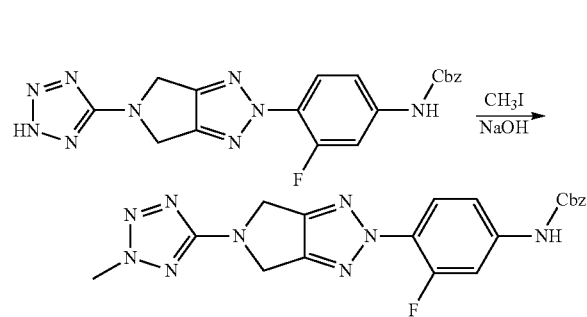

The procedure was the same as Example 6 (2), at a yield of 18.1%.

(3) Preparation of (R)-(3-(3-fluoro-4-(5-(2-methyl-2H-tetrazol-5-yl)-5,6-dihydropyrrolo[3,4-d][1,2,3]triazol-2 (4H)-yl)phenyl)-5-(hydroxylmethyl)oxazolidin-2-one

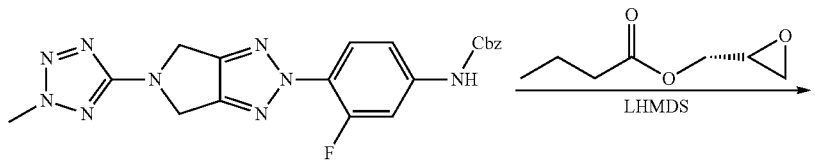

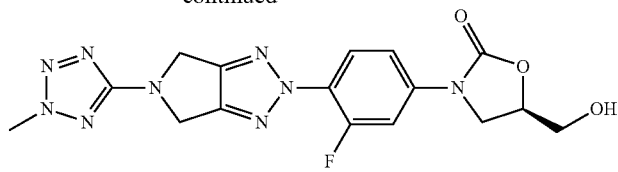

The procedure was the same as Example 6 (5), at a yield of 15.5%.

Molecular formula: $C_{16}H_{16}FN_9O_3$ Molecular weight: 401.4 Mass spectrum (m/e): 402.1 (M+H)

$^1$H-NMR (400 MHz, DMSO-$d_6$) δ: 7.805 (m, 1H), 7.799 (m, 1H), 7.569 (d, 1H), 5.258 (t, 1H), 4.745 (m, 1H), 4.709 (s, 4H), 4.216 (s, 3H), 4.144 (m, 1H), 3.886 (m, 1H), 3.700 (m, 1H), 3.586 (m, 1H).

Example 8

Preparation of (R)-(3-(3-fluoro-4-(5-(1-methyl-1H-tetrazol-5-yl)-5,6-dihydropyrrolo[3,4-d][1,2,3]triazol-2(4H)-yl)phenyl)-5-(hydroxylmethyl)oxazolidin-2-one (Compound 16)

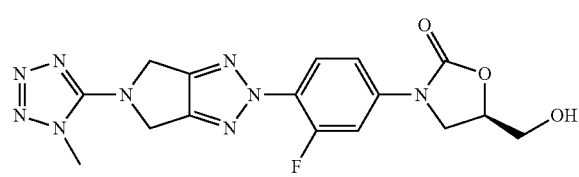 [SMILES: Cn1nnnc1N1Cc2nn(-c3ccc(N4C[C@H](CO)OC4=O)cc3F)nc2C1]

(1) Benzyl 4-(5-(2H-tetrazol-5-yl)-5,6-dihydropyrrolo[3,4-d][1,2,3]triazol-2(4H)-yl)-3-fluorophenylcarbamate

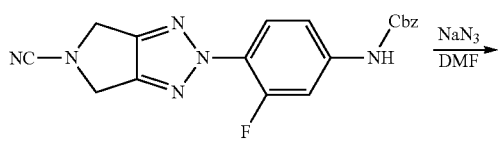

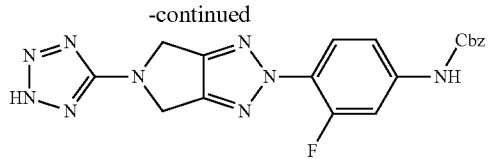

The procedure was the same as Example 6 (1). The product was used directly for the next step of reaction without purification.

(2) Benzyl 3-fluoro-4-(5-(1-methyl-1H-tetrazol-5-yl)-5,6-dihydropyrrolo[3,4-d][1,2,3]triazol-2(4H)-yl)phenylcarbamate

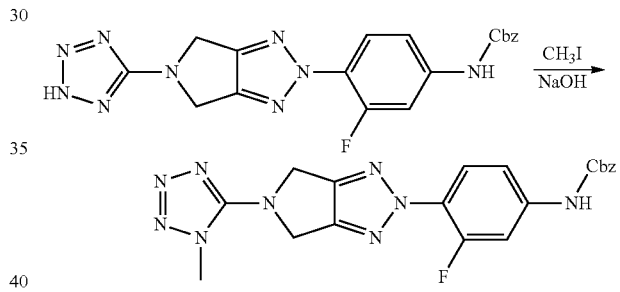

The procedure was the same as Example 6 (2), at a yield of 13%.

(3) Preparation of (R)-(3-(3-fluoro-4-(5-(1-methyl-1H-tetrazol-5-yl)-5,6-dihydropyrrolo[3,4-d][1,2,3]triazol-2(4H)-yl)phenyl)-5-(hydroxylmethyl)oxazolidin-2-one

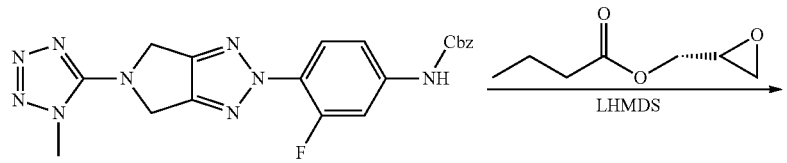

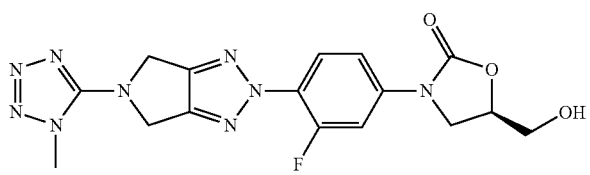

The procedure was the same as Example 6 (5), at a yield of 23%.

Molecular formula: $C_{16}H_{16}FN_9O_3$ Molecular weight: 401.3 Mass spectrum (m/e): 402.1 (M+H)

$^1$H-NMR (400 MHz, DMSO-d$_6$) δ: 7.853 (m, 1H), 7.807 (m, 1H), 7.577 (d, 1H), 5.259 (t, 1H), 4.978 (s, 4H), 4.750 (m, 1H), 4.218 (s, 3H), 4.108 (m, 1H), 3.897 (m, 1H), 3.688 (m, 1H), 3.590 (m, 1H).

Example 9

Preparation of (R)-(3-(3-fluoro-4-(2-(1-methyl-1H-imidazol-2-yl) isoindolin-5-yl)phenyl)-5-(hydroxyl-methyl)oxazolidin-2-one (Compound 17)

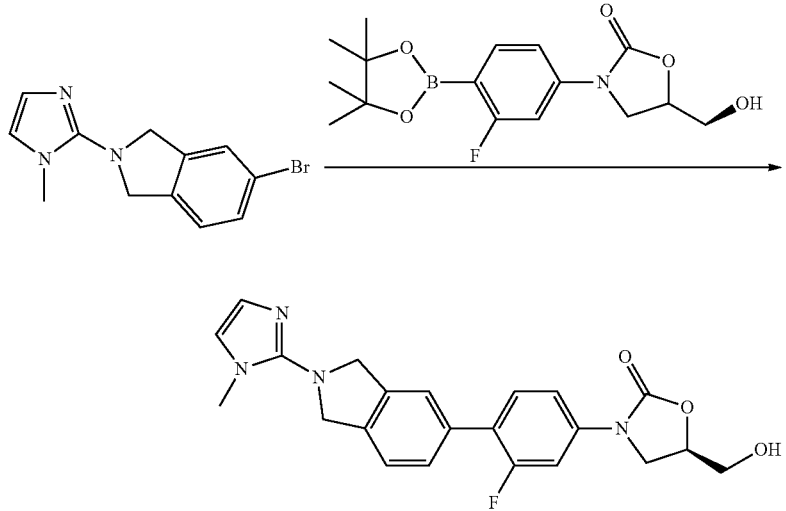

The procedure was the same as Example 1 (2), at a yield of 22%.

Molecular formula: $C_{22}H_{21}FN_4O_3$ Molecular weight: 408.4 Mass spectrum (m/e): 409.2 (M+H)

$^1$H-NMR (400 MHz, DMSO-d$_6$) δ: 7.56 (d, 1H), 7.49 (t, 1H), 7.45 (s, 1H), 7.431 (m, 3H), 6.82 (d, 1H), 6.57 (d, 1H), 5.24 (t, 1H), 4.47 (m, 5H), 4.13 (t, 1H), 3.89 (t, 1H), 3.72 (m, 1H), 3.60 (m, 1H), 3.59 (s, 3H).

Example 10

Preparation of (R)-(3-(4-(2-(1H-imidazol-2-yl)isoindolin-5-yl)-3-fluorophenyl)-5-(hydroxylmethyl)oxazolidin-2-one (Compound 18)

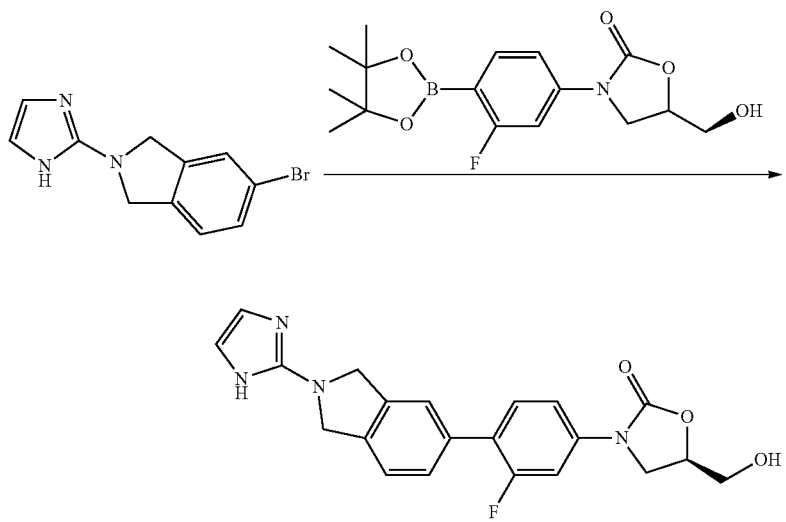

The procedure was the same as Example 1 (2), at a yield of 31%.

Molecular formula: $C_{21}H_{19}FN_4O_3$ Molecular weight: 394.4 Mass spectrum (m/e): 395.1 (M+H)

$^1$H-NMR (400 MHz, DMSO-$d_6$) δ: 12.5 (br s, 1H), 7.65 (m, 3H), 7.60 (s, 2H), 7.45 (d, 1H), 7.16 (s, 2H), 5.26 (t, 1H), 4.85 (s, 4H), 4.74 (m, 1H), 4.13 (t, 1H), 3.89 (m, 1H), 3.69 (m, 1H), 3.55 (m, 1H).

Example 11

Preparation of (R)-(3-(3-fluoro-4-(2-(1-methyl-1H-tetrazol-5-yl) isoindolin-5-yl)-phenyl)-5-(hydroxyl-methyl)oxazolidin-2-one (Compound 19)

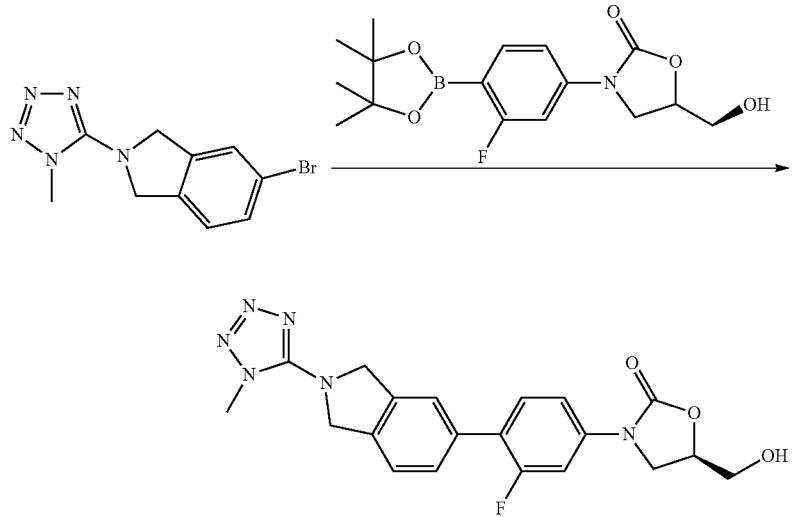

The procedure was the same as Example 1 (2), at a yield of 60.9%.

Molecular formula: $C_{20}H_{19}FN_6O_3$ Molecular weight: 410.4 Mass spectrum (m/e): 411.2 (M+H)

$^1$H-NMR (400 MHz, DMSO-$d_6$) δ: 7.45-7.62 (m, 6H), 5.25 (m, 1H), 5.02 (s, 4H), 4.74 (m, 1H), 4.13 (m, 4H), 3.88 (m, 1H), 3.67 (m, 1H), 3.55 (m, 1H).

Example 12

Preparation of (R)-(3-(4-(2-(1H-pyrazol-5-yl)isoindolin-5-yl)-3-fluorophenyl)-5-(hydroxylmethyl)oxazolidin-2-one (Compound 20)

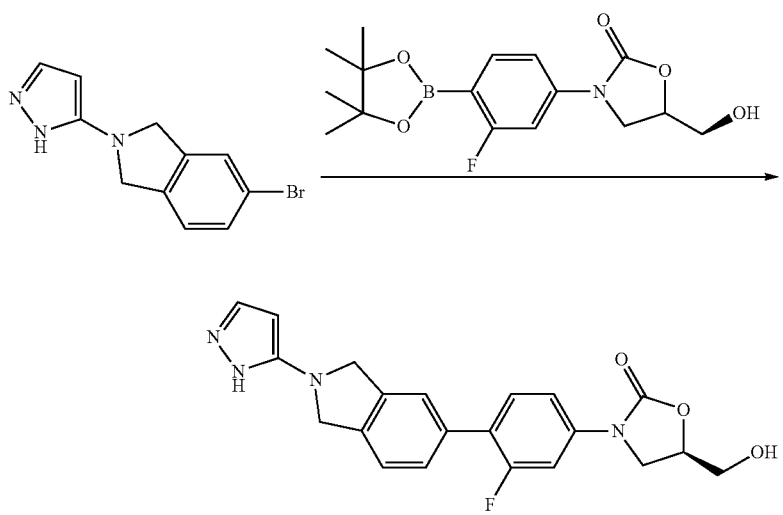

The procedure was the same as Example 1 (2), at a yield of 22%.

Molecular formula: $C_{21}H_{19}FN_4O_3$ Molecular weight: 394.4 Mass spectrum (m/e): 395.2 (M+H)

$^1$H-NMR (400 MHz, DMSO-d$_6$) δ: 11.8 (s, 1H), 7.45-7.62 (m, 7H), 5.65 (s, 1H), 5.25 (t, 1H), 4.74 (m, 1H), 4.55 (s, 4H), 4.13 (t, 1H), 3.88 (m, 1H), 3.67 (m, 1H), 3.55 (m, 1H).

Example 13

Preparation of (R)-3-(3-fluoro-(4-(2-(1-methyl-1H-pyrazol-5-yl) isoindolin-5-yl)phenyl)-5-(hydroxylmethyl) oxazolidin-2-one (Compound 21)

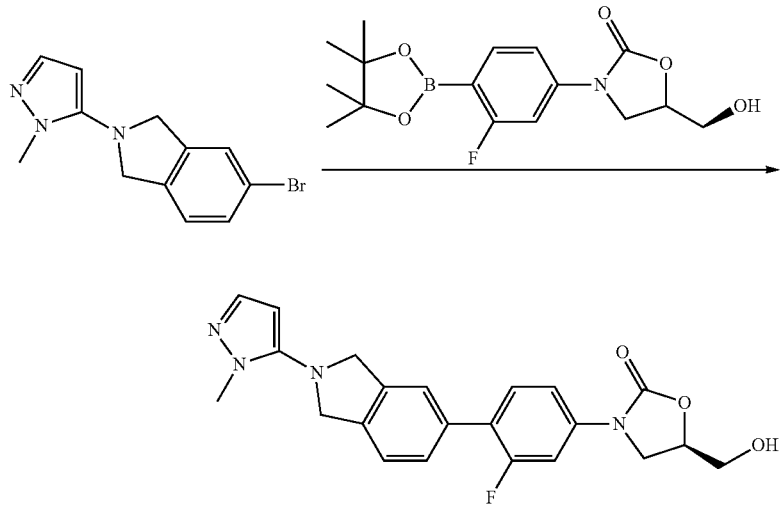

The procedure was the same as Example 1 (2), at a yield of 8.3%.

Molecular formula: $C_{22}H_{21}FN_4O_3$ Molecular weight: 408.4 Mass spectrum (m/e): 409.2 (M+H)

$^1$H-NMR (400 MHz, DMSO-d$_6$) δ: 7.62 (d, 1H), 7.56 (t, 1H), 7.49 (s, 1H), 7.43 (s, 3H), 7.27 (s, 1H), 7.23 (s, 1H), 5.81 (s, 1H), 5.25 (t, 1H), 4.73 (s, 1H), 4.58 (s, 4H), 4.47-4.49 (m, 1H), 4.12 (t, 1H), 3.87 (t, 1H), 3.77 (s, 3H), 3.70 (s, 1H), 3.55-3.59 (m, 1H).

Example 14

Preparation of (R)-3-(3-fluoro-(4-(2-(1-methyl-1H-pyrazol-3-yl) isoindolin-5-yl)phenyl)-5-(hydroxylmethyl)oxazolidin-2-one (Compound 22)

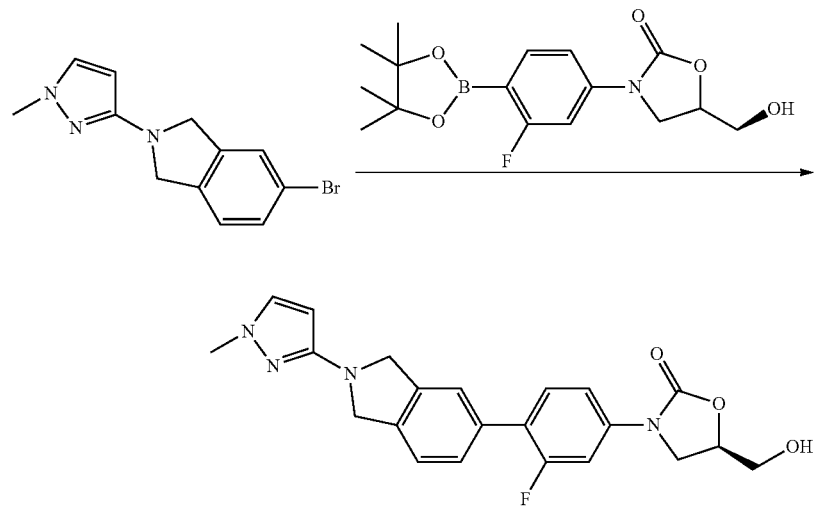

The procedure was the same as Example 1 (2), at a yield of 33%.

Molecular formula: $C_{22}H_{21}FN_4O_3$ Molecular weight: 408.4 Mass spectrum (m/e): 409.2 (M+H)

$^1$H-NMR (400 MHz, DMSO-$d_6$) δ: 7.64 (d, 1H), 7.60 (d, 1H), 7.50 (s, 1H), 7.43-7.46 (m, 4H), 5.58 (s, 1H), 5.24 (t, 1H), 4.73 (m, 1H), 4.52 (s, 4H), 4.12 (t, 1H), 3.87 (t, 1H), 3.68 (s, 3H), 3.66 (m, 1H), 3.58 (m, 1H).

Example 15

Preparation of (R)-3-(3-fluoro-(4-(2-(2-methyl-2H-1,2,3-triazol-4-yl) isoindolin-5-yl)phenyl)-5-(hydroxylmethyl) oxazolidin-2-one (Compound 23)

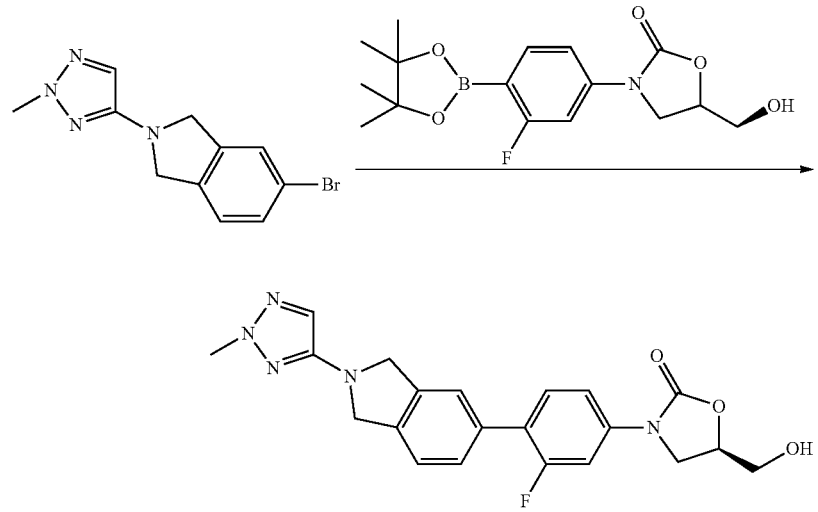

The procedure was the same as Example 1 (2), at a yield of 21%.

Molecular formula: $C_{21}H_{20}FN_5O_3$ Molecular weight: 409.4 Mass spectrum (m/e): 410.2 (M+H)

$^1$H-NMR (400 MHz, DMSO-$d_6$) δ: 7.64 (d, 1H), 7.60 (d, 1H), 7.52 (d, 1H), 7.46 (m, 3H), 7.16 (s, 1H), 5.23 (t, 1H), 4.73 (m, 1H), 4.59 (s, 4H), 4.12 (t, 1H), 3.99 (s, 3H), 3.85 (m, 1H), 3.66 (m, 1H), 3.58 (m, 1H).

Example 16

Preparation of (R)-3-(3-fluoro-(4-(2-(1-methyl-1H-1,2,3-triazol-4-yl) isoindolin-5-yl)phenyl)-5-(hydroxylmethyl)oxazolidin-2-one (Compound 24)

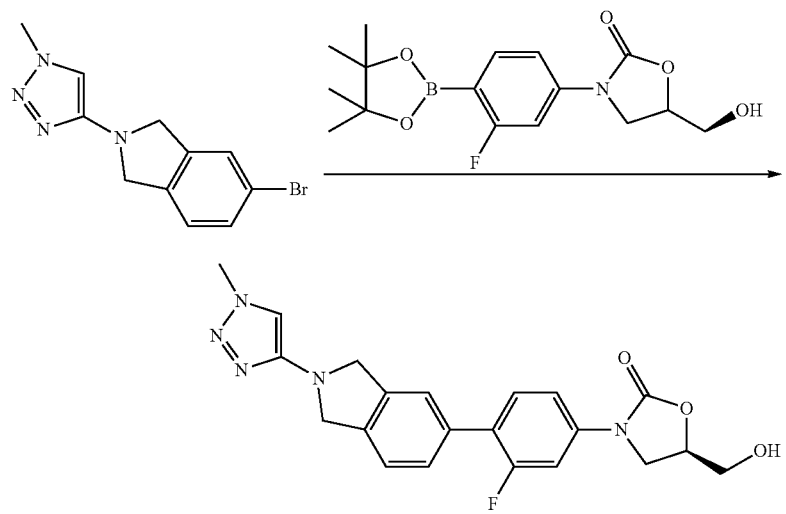

The procedure was the same as Example 1 (2), at a yield of 14%.

Molecular formula: $C_{21}H_{20}FN_5O_3$ Molecular weight: 409.4 Mass spectrum (m/e): 410.2 (M+H)

$^1$H-NMR (400 MHz, DMSO-d$_6$) δ: 7.64 (d, 1H), 7.60 (m, 2H), 7.46 (m, 3H), 7.39 (s, 1H), 5.23 (t, 1H), 4.73 (m, 1H), 4.56 (s, 4H), 4.13 (t, 1H), 3.96 (s, 3H), 3.88 (m, 1H), 3.70 (m, 1H), 3.58 (m, 1H).

Example 17

Preparation of (R)-(3-(4-(2-(1H-1,2,3-triazol-5-yl)isoindolin-5-yl)-3-fluorophenyl)-2-oxo-oxazolidin-5-yl)methyl phosphate disodium salt (Compound 26)

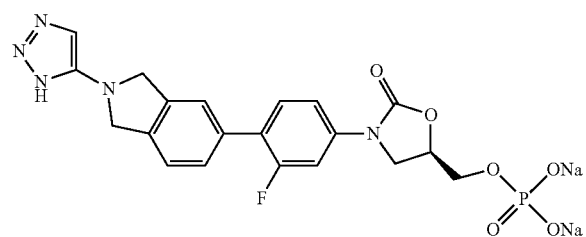

(1) Preparation of (R)-(3-(4-(2-(1H-1,2,3-triazol-5-yl)isoindolin-5-yl)-3-fluorophenyl)-2-oxo-oxazolidin-5-yl)methyl dihydrogen phosphate

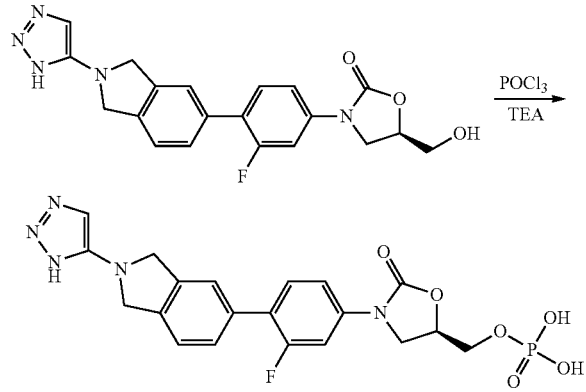

(R)-3-fluoro-4-(6-((1-methyl-1H-tetrazol-5-yl)amino)pyridin-3-yl)phenyl)-5-(hydroxylmethyl)oxazolidin-2-one, (R)-3-(4-(2-(1H-1,2,3-triazol-5-yl)isoindolin-5-yl)-3-fluorophenyl)-5-(hydroxylmethyl)oxazolidin-2-one (200 mg, 0.51 mmol) were dissolved in 30 mL THF. Triethylamine (262 mg, 2.6 mmol) was added under ice-water bath. After 0.5 hour, phosphorus oxychloride (397 mg, 2.6 mmol) was added, and reacted for 12 h at room temperature. Water (180 mg, 10 mmol) was added dropwise. By filtration, 100 mg of product was obtained, at a yield of 41%.

(2) Preparation of (R)-(3-(4-(2-(1H-1,2,3-triazol-5-yl)isoindolin-5-yl)-3-fluorophenyl)-2-oxo-oxazolidin-5-yl)methyl phosphate disodium salt

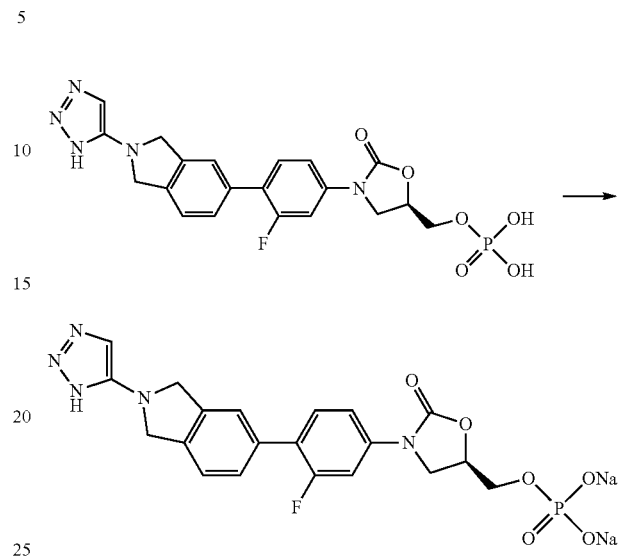

(R)-(3-(4-(2-(1H-1,2,3-triazol-5-yl)isoindolin-5-yl)-3-fluorophenyl)-2-oxo-oxazolidin-5-yl)methyl dihydrogen phosphate (100 mg, 0.21 mmol) was dissolved in 15 mL methanol. Sodium methoxide (48 mg, 0.9 mmol) was added, and reacted for 12 h at room temperature. By filtration, 85 mg of product was obtained, at a yield of 78%.

Molecular formula: $C_{20}H_{17}FN_5Na_2O_6P$ Mass spectrum (m/e): 520.1 (M+1)

Example 18

Preparation of (R)-(3-(3-fluoro-4-(5-(2-methyl-2H-tetrazol-5-yl)-5,6-dihydropyrrole[3,4-d]-[1,2,3]triazol-2(4H)-yl)phenyl)-2-oxo-oxazolidin-5-yl)methyl phosphate disodium salt (Compound 27)

The procedure was the same as Example 17, at a yield of 72%.

Molecular formula: $C_{16}H_{15}FN_9Na_2O_6P$ Molecular weight: 525.3 Mass spectrum (m/e): 526.1 (M+H)

Example 19

Preparation of (R)-(3-(4-(2-(1H-imidazol-2-yl)isoindolin-5-yl)-3-fluorophenyl)-2-oxo-oxazolidin-5-yl)methyl phosphate disodium salt (Compound 28)

Example 20

Preparation of (R)-(3-(3-fluoro-4-(2-(1-methyl-1H-tetrazol-5-yl) isoindolin-5-yl)phenyl)-2-oxo-oxazolidin-5-yl)methyl phosphate disodium salt (Compound 29)

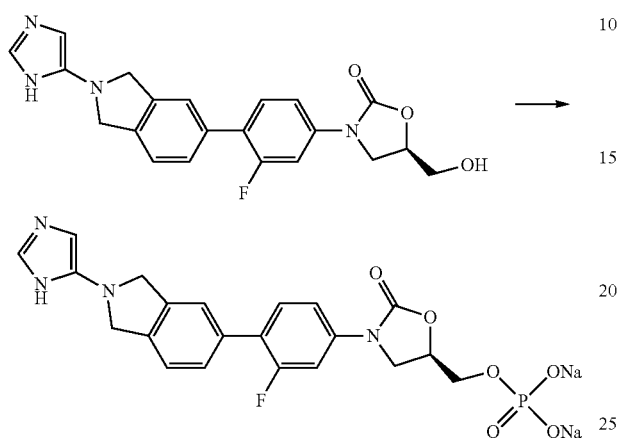

The procedure was the same as Example 17, at a yield of 75%.

Molecular formula: $C_{21}H_{18}FN_4Na_2O_6P$ Molecular weight: 518.3 Mass spectrum (m/e): 519.1 (M+H)

The procedure was the same as Example 17, at a yield of 77%.

Molecular formula: $C_{20}H_{18}FN_6Na_2O_6P$ Molecular weight: 534.4 Mass spectrum (m/e): 535.1 (M+H)

In accordance with the above preparation methods, the following compounds can also be prepared:

| Compound | Structural Formula |
| --- | --- |
| 31 | |
| 32 | |
| 33 | |
| 34 | |

| Compound | Structural Formula |
|---|---|
| 35 | 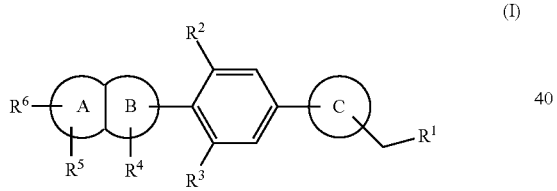 |
| 36 | |
| 37 | |

The invention claimed is:

1. A compound as shown by general formula (I), a pharmaceutically acceptable salt thereof, an stereoisomer thereof or a prodrug thereof:

(I)

wherein,
$R^1$ is selected from —$OR^7$, —$NR^7R^{7'}$, —$COR^7$, —$COOR^7$, —$OCOR^7$, —$CONR^7R^{7'}$, —$NR^7COR^{7'}$, —$OCONR^7R^{7'}$, —$NR^7COOR^{7'}$, and —$NR^7CONR^{7'}R^7$, wherein $R^7$ and $R^{7'}$ are independently selected from: H, $C_{1-6}$ alkyl, $C_{2-6}$ alkenyl, and $C_{2-6}$ alkynyl;

$R^2$ and $R^3$ are independently selected from hydrogen, halogen, $C_{1-6}$ alkyl, $C_{1-6}$ alkyl-amino, di($C_{1-6}$ alkyl) amino, and $C_{1-6}$ alkoxyl;

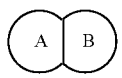

is a fused condensed bicyclic system formed by ring A and ring B together, wherein ring A is a 3-8 membered cyclic group, which is unsubstituted or substituted by 1-3 $R^5$, wherein $R^5$ is independently selected from hydrogen, halogen, $C_{1-6}$ alkyl, halo$C_{1-6}$ alkyl, hydroxyl, hydroxyl$C_{1-6}$ alkyl, amino, $C_{1-6}$ alkylamino, di($C_{1-6}$ alkyl)amino, and $C_{1-6}$ alkylcarbamyl;

ring B is a phenyl ring, which is unsubstituted or substituted by 1-3 $R^4$, wherein $R^4$ is selected from hydrogen, halogen, $C_{1-6}$ alkyl, halo$C_{1-6}$ alkyl, hydroxyl, hydroxyl$C_{1-6}$ alkyl, amino, $C_{1-6}$ alkylamino, di($C_{1-6}$ alkyl) amino, and $C_{1-6}$ alkylcarbamyl;

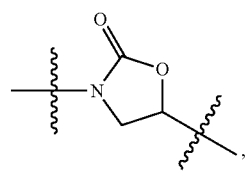 [SMILES: *C1CN(*)C(=O)O1]

ring C is
and
$R^6$ is a 5-14 membered heteroaryl which is unsubstituted or substituted by 1-3 $R^8$;

$R^8$ being selected from halogen, carboxyl, hydroxyl, amino, cyano, nitro, $C_{1-6}$ alkyl, carboxyl$C_{1-6}$ alkyl, hydroxyl$C_{1-6}$ alkyl, amino$C_{1-6}$ alkyl, halo$C_{1-6}$ alkyl, $C_{1-6}$ alkoxyl, halo$C_{1-6}$ alkoxyl, $C_{1-6}$ alkoxyl$C_{1-6}$ alkyl, $C_{1-6}$ alkylamino, di($C_{1-6}$ alkyl)amino, di($C_{1-6}$ alkyl) amino$C_{1-6}$ alkyl, $C_{1-6}$ alkylcarbonyl, $C_{1-6}$ alkylcarbonyloxy, $C_{1-6}$ alkoxylcarbonyl, carbamyl, carbamyl$C_{1-6}$ alkyl, $C_{1-6}$ alkylcarbamyl, di($C_{1-6}$ alkyl)carbamyl, aminosulfonyl, aminosulfonyl$C_{1-6}$ alkyl, $C_{1-6}$ alkylaminosulfonyl, di($C_{1-6}$ alkyl)aminosulfonyl, $C_{1-6}$ alkylsulfonylamino, $C_{1-6}$ alkylsulfonyl, $C_{1-6}$ alkylcarbonylamino, and guanidino.

2. The compound of claim 1, a pharmaceutically acceptable salt thereof, an stereoisomer thereof or a prodrug thereof, having a structure of general formula (II):

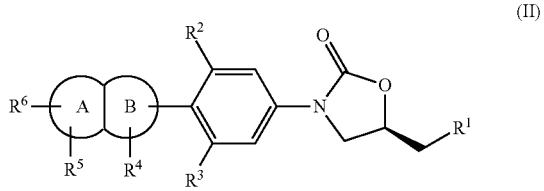

(II)

wherein, $R^1$, $R^2$, $R^3$, $R^4$, $R^5$, $R^6$ and

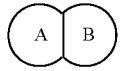

are as defined in claim 1.

3. The compound of claim 1, a pharmaceutically acceptable salt thereof, an stereoisomer thereof or a prodrug thereof:
wherein,
$R^1$ is acetylamino or hydroxyl;
$R^2$ and $R^3$ are independently selected from hydrogen and halogen;
ring A is a 5-6 membered cycloalkyl or 5-6 membered heterocyclyl, which are unsubstituted or substituted by 1-2 $R^5$, wherein $R^5$ is independently selected from hydrogen, halogen, $C_{1-4}$ alkyl, halo$C_{1-4}$ alkyl, hydroxyl, hydroxyl$C_{1-4}$ alkyl, amino, $C_{1-4}$ alkylamino, di($C_{1-4}$ alkyl)amino and $C_{1-4}$ alkylcarbamyl;
ring B is a phenyl ring, which is unsubstituted or substituted by 1-2 $R^4$, wherein $R^4$ is independently selected from hydrogen, halogen, $C_{1-4}$ alkyl, halo$C_{1-4}$ alkyl, hydroxyl, hydroxyl$C_{1-4}$ alkyl, amino, $C_{1-4}$ alkylamino, di($C_{1-4}$ alkyl)amino, and $C_{1-4}$ alkylcarbamyl; and
$R^6$ is a 5-6 membered heteroaryl containing 1, 2, 3 or 4 N atoms, which is unsubstituted or substituted by 1-2 $R^8$, wherein $R^8$ is a $C_{1-4}$ alkyl which is unsubstituted or substituted by halogen.

4. The compound of claim 3, a pharmaceutically acceptable salt thereof, an stereoisomer thereof or a prodrug thereof:
wherein,
$R^1$ is acetylamino or hydroxyl;
$R^2$ and $R^3$ are independently selected from hydrogen and fluoro;
ring A is selected from the following groups which are unsubstituted or substituted by 1-2 $R^5$: cyclopentyl, cyclohexyl, tetrahydropyrrolyl, 2,3-dihydropyrrolyl, 2,5-dihydropyrrolyl, pyrrolyl, imidazolyl, 4,5-dihydroimidazolyl, pyrazolyl, 4,5-dihydropyrazolyl, 1,2,3-triazolyl, tetrahydrothienyl, thienyl, 2,3-dihydrothienyl, thiazolyl, 4,5-dihydrothiazolyl, isothiazolyl, tetrahydrofuryl, 2,3-dihydrofuryl, furyl, 4,5-dihydrooxazolyl, oxazolyl, 4,5-dihydroisoxazolyl, isoxazolyl, phenyl ring, 1,4,5,6-tetrahydropyrimidinyl, 1,6-dihydropyrimidinyl, 4,5-dihydropyrimidinyl, pyrimidinyl, 3,6-dihydro-2H-pyranyl, 2H-pyranyl, piperidyl, 1,2,3,4-tetrahydropyridyl, 1,2,3,6-tetrahydropyridyl, 2,3-dihydropyridyl, pyridyl, piperazinyl, 1,2,3,4-tetrahydropyrazinyl, 2,3-dihydropyrazinyl and pyrazinyl group, wherein $R^5$ is independently selected from hydrogen, fluoro, methyl, trifluoromethyl, hydroxyl, hydroxylmethyl, amino, methylamino, ethylamino, methylcarbamyl, and ethylcarbamyl;
ring B is a phenyl ring, which is unsubstituted or substituted by 1-2 $R^4$, wherein $R^4$ is selected from hydrogen, fluoro, methyl, fluoromethyl, trifluoromethyl, hydroxyl, hydroxylmethyl, amino, methylamino, ethylamino, methylcarbamyl, and ethylcarbamyl; and
$R^6$ is selected from the following groups which are unsubstituted or substituted by 1-2 $R^8$: pyrrolyl, imidazolyl, pyrazolyl, 1,2,3-triazolyl, 1,2,4-triazolyl, 1,2,3,4-tetrazolyl, pyridyl and pyrazinyl, wherein $R^8$ is selected from methyl, ethyl, propyl, and trifluoromethyl.

5. The compound of claim 4, a pharmaceutically acceptable salt thereof, an stereoisomer thereof or a prodrug thereof:
wherein,
$R^1$ is acetylamino or hydroxyl;
$R^2$ and $R^3$ are independently selected from hydrogen, and fluoro;
ring A is selected from the following groups which are unsubstituted or substituted by 1-2 $R^5$: cyclopentyl, cyclohexyl, tetrahydropyrrolyl, 2,3-dihydropyrrolyl, 2,5-dihydropyrrolyl, pyrrolyl, imidazolyl, 4,5-dihydroimidazolyl, pyrazolyl, 4,5-dihydropyrazolyl, 1,2,3-triazolyl, tetrahydrothienyl, thienyl, 2,3-dihydrothienyl, thiazolyl, 4,5-dihydrothiazolyl, isothiazolyl, tetrahydrofuryl, 2,3-dihydrofuryl, furyl, 4,5-dihydrooxazolyl, oxazolyl, 4,5-dihydroisoxazolyl, isoxazolyl, phenyl ring, 1,4,5,6-tetrahydropyrimidinyl, 1,6-dihydropyrimidinyl, 4,5-dihydropyrimidinyl, pyrimidinyl, 3,6-dihydro-2H-pyranyl, 2H-pyranyl, piperidyl, 1,2,3,4-tetrahydropyridyl, 1,2,3,6-tetrahydropyridyl, 2,3-dihydropyridyl, pyridyl, piperazinyl, 1,2,3,4-tetrahydropyrazinyl, 2,3-dihydropyrazinyl and pyrazinyl group, wherein $R^5$ is independently selected from hydrogen, fluoro, methyl, trifluoromethyl, hydroxyl, hydroxylmethyl, amino, methylamino, ethylamino, methylcarbamyl, and ethylcarbamyl;
ring B is a phenyl ring, which is unsubstituted or substituted by 1-2 $R^4$, wherein $R^4$ is selected from hydrogen, fluoro, methyl, fluoromethyl, trifluoromethyl, hydroxyl, hydroxylmethyl, amino, methylamino, ethylamino, methylcarbamyl, and ethylcarbamyl; and
$R^6$ is selected from the following groups which are unsubstituted or substituted by 1-2 $R^8$: pyrrolyl, imidazolyl, pyrazolyl, 1,2,3-triazolyl, 1,2,4-triazolyl, 1,2,3,4-tetrazolyl, pyridyl and pyrazinyl, wherein $R^8$ is selected from methyl, ethyl, propyl, and trifluoromethyl.

6. The compound of claim 5, a pharmaceutically acceptable salt thereof, an stereoisomer thereof or a prodrug thereof:
wherein,
$R^1$ is acetylamino or hydroxyl;
$R^2$ and $R^3$ are independently selected from hydrogen and fluoro;
ring A is selected from the following groups which are unsubstituted or substituted by 1-2 $R^5$: cyclopentyl, cyclohexyl, tetrahydropyrrolyl, 2,3-dihydropyrrolyl, 2,5-dihydropyrrolyl, pyrrolyl, imidazolyl, 4,5-dihydroimidazolyl, pyrazolyl, 4,5-dihydropyrazolyl, 1,2,3-triazolyl, tetrahydrothienyl, thienyl, 2,3-dihydrothienyl, thiazolyl, 4,5-dihydrothiazolyl, tetrahydrofuryl, 2,3-dihydrofuryl, furyl, oxazolyl, phenyl ring, 1,4,5,6-tetrahydropyrimidinyl, 1,6-dihydropyrimidinyl, 4,5-dihydropyrimidinyl, pyrimidinyl, 3,6-dihydro-2H-pyranyl, 2H-pyranyl, piperidyl, 1,2,3,4-tetrahydropyridyl, 1,2,3,6-tetrahydropyridyl, 2,3-dihydropyridyl, pyridyl, piperazinyl, 1,2,3,4-tetrahydropyrazinyl, 2,3-dihydropyrazinyl, and pyrazinyl group, wherein R⁵ is selected from hydrogen, fluoro, methyl, and methylcarbamyl;

ring B is a phenyl ring, which is unsubstituted or substituted by 1-2 R⁴, wherein R⁴ is selected from hydrogen, fluoro, methyl, and fluoromethyl; and R⁶ is selected from pyrazolyl, imidazolyl, 1,2,3-triazolyl, 1,2,4-triazolyl, and 1,2,3,4-tetrazolyl, which are unsubstituted or substituted by 1-2 R⁸, wherein R⁸ is selected from methyl and ethyl.

7. The compound of claim 5, a pharmaceutically acceptable salt thereof, an stereoisomer thereof or a prodrug thereof, the compound being selected from:

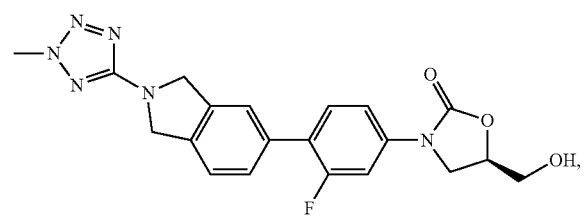

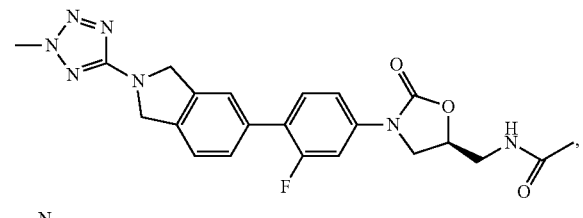

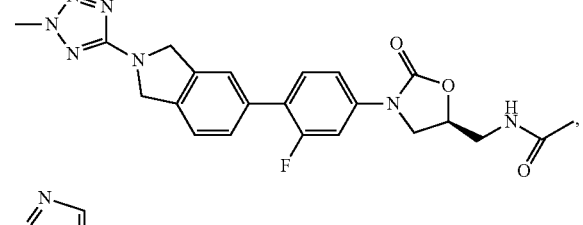

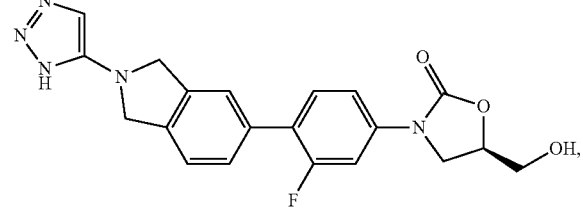

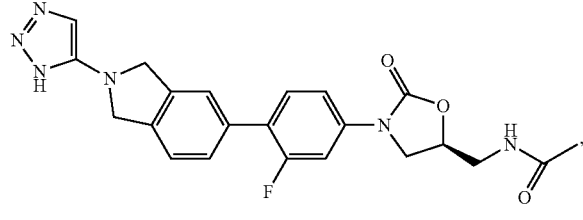

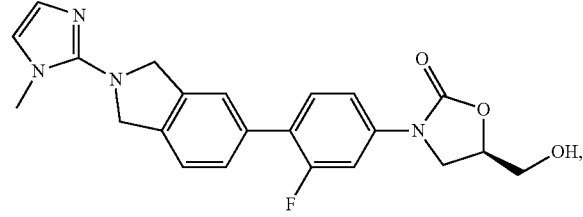

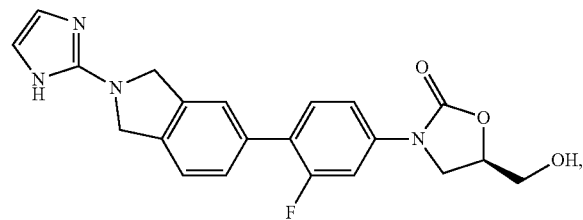

-continued

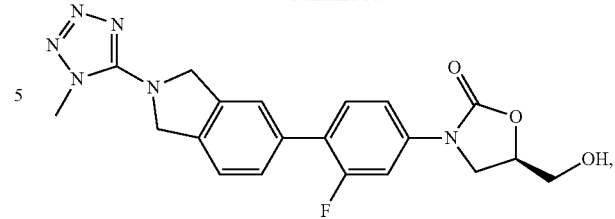

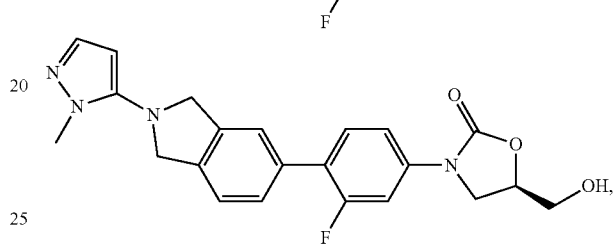

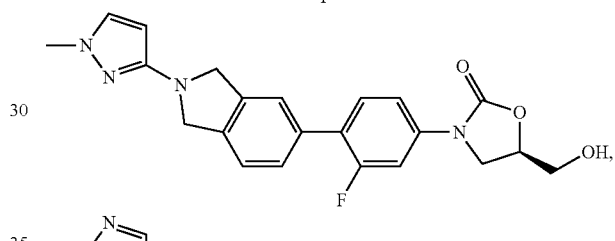

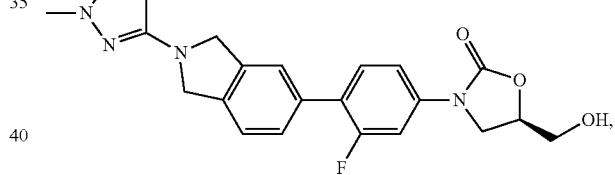

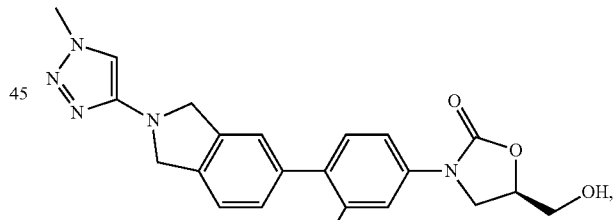

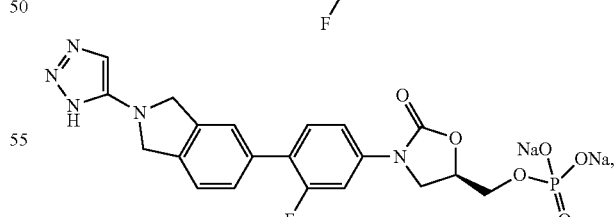

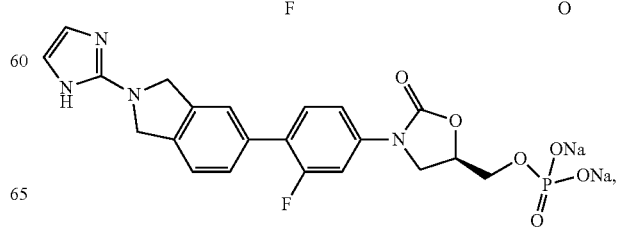

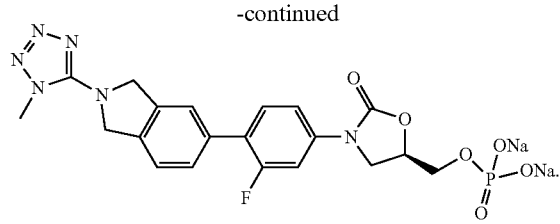

8. A pharmaceutical composition, comprising the compound of claim 1, a pharmaceutically acceptable salt thereof, an stereoisomer thereof or a prodrug thereof, and one more pharmaceutically acceptable carriers and/or diluents.

9. A pharmaceutical formulation, comprising the compound of claim 1, a pharmaceutically acceptable salt thereof, an stereoisomer thereof or a prodrug thereof, and one or more pharmaceutically acceptable carriers and/or diluents, which can be made into any clinically or pharmaceutically acceptable dosage form.

10. A method of use of compound of claim 1, a pharmaceutically acceptable salt thereof, a stereoisomer thereof or a prodrug thereof for the treatment of infectious diseases.

* * * * *